United States Patent [19]
Milliman et al.

[11] Patent Number: 6,036,657
[45] Date of Patent: Mar. 14, 2000

[54] APPARATUS FOR REMOVING TISSUE

[75] Inventors: Keith L. Milliman, Bethel; Lisa W. Heaton, Norwalk, both of Conn.

[73] Assignee: United States Surgical Corporation, Norwalk, Conn.

[21] Appl. No.: 09/178,730

[22] Filed: Oct. 26, 1998

Related U.S. Application Data

[63] Continuation of application No. 08/525,450, Sep. 8, 1995, Pat. No. 5,857,982.

[51] Int. Cl.⁷ .................................................. A61B 10/00
[52] U.S. Cl. ........................................... 600/564; 604/170
[58] Field of Search .................................. 600/562, 564, 600/567; 604/170

[56] References Cited

U.S. PATENT DOCUMENTS

| | | |
|---|---|---|
| 254,154 | 2/1882 | Perez et al. . |
| 417,797 | 12/1979 | Baylis et al. . |
| 1,568,008 | 12/1925 | Thomas et al. . |
| 1,609,456 | 12/1926 | Boyle . |

(List continued on next page.)

FOREIGN PATENT DOCUMENTS

| | | |
|---|---|---|
| 653191 | 5/1995 | European Pat. Off. . |
| 761170 | 3/1997 | European Pat. Off. . |
| 2610508 | 10/1987 | France . |
| 263228 | 8/1987 | Germany . |
| 534505 | 6/1970 | Switzerland . |
| WO 8201988 | 6/1982 | WIPO . |
| WO 9724070 | 7/1997 | WIPO . |

OTHER PUBLICATIONS

Mechcatie, E., Stereotactic Breast Biopsies Effective, Less Expensive Than Surgery, OB Gyn, Jul. 15, 1994, at 10.

Lorad, Designing the Future of Breast Biopsy, Product brochure, published before Applicants' filing date.

Biopsys; Medical Inc., The Single–Insertion Mammotome™ Biopsy System, BMI–3473, Feb. 1995, p. 500.

Mitnick et al., Stereotaxic Localization for Fine–Needle Aspiration Breast Biopsy, Arch. Surg., vol. 126, Sep. 1991.

Article: Elizabeth Mechcatie, Stereotactic Breast Biopsies Effective, Less Expensive Than Surgery, OB Gyn News, Jul. 15, 1994.

Lorad, Designing the Future of Breast Biopsy.

*Primary Examiner*—Cary O'Connor
*Assistant Examiner*—Pamela L. Wingood

[57] ABSTRACT

A surgical apparatus for removing tissue, which includes a housing, an elongated body which extends from the housing and forms an opening at a distal end, the elongated body further forming a tissue receiving cavity in communication with the opening, a cutting member operatively associated with the housing and movable transverse to the elongated body in proximity to the opening, and a tissue retaining member positioned in proximity to the opening and the cutting member, the retaining member being selectively movable from a retracted position to a deployed position, wherein when positioned in the deployed position, the tissue retaining member obstructs at least a portion of the opening at the distal end of the elongated body. A method is also provided for surgically removing tissue including the steps of positioning a tissue removing instrument including an elongated housing having a tissue receiving cavity at a distal end, a first tissue cutting surface longitudinally movable relative to the elongated housing distal end, an obturator having a sharpened distal end portion such that the sharpened end portion is positioned adjacent the tissue to be removed and a second tissue cutting surface transversely movable relative to the elongated housing, removing the obturator from the elongated housing, coring the tissue to be removed, severing the cored tissue from the surrounding tissue with the second cutting surface, and removing the severed tissue from the patient.

15 Claims, 20 Drawing Sheets

U.S. PATENT DOCUMENTS

| | | |
|---|---|---|
| 1,615,494 | 1/1927 | Waring . |
| 2,117,278 | 5/1938 | Ainsworth . |
| 2,514,665 | 7/1950 | Myller ........................................ 600/570 |
| 3,470,867 | 10/1969 | Goldsmith . |
| 3,477,423 | 11/1969 | Griffith . |
| 3,605,721 | 9/1971 | Hallac . |
| 3,628,524 | 12/1971 | Jamshidi . |
| 4,010,737 | 3/1977 | Vilaghy et al. . |
| 4,099,518 | 12/1979 | Baylis et al. . |
| 4,174,715 | 11/1979 | Hasson . |
| 4,306,570 | 12/1981 | Matthews . |
| 4,461,305 | 7/1984 | Cibley . |
| 4,651,752 | 3/1987 | Fuerst . |
| 4,678,459 | 7/1987 | Onik et al. . |
| 4,776,346 | 10/1988 | Beraha et al. . |
| 4,785,826 | 11/1988 | Ward . |
| 4,817,631 | 4/1989 | Schnepp-Pesch et al. . |
| 4,850,373 | 7/1989 | Zatloukal et al. . |
| 4,881,550 | 11/1989 | Kothe . |
| 4,926,877 | 5/1990 | Bookwalter . |
| 4,940,061 | 7/1990 | Terwilliger et al. . |
| 4,958,625 | 9/1990 | Bates et al. . |
| 4,971,067 | 11/1990 | Bolduc et al. . |
| 4,989,614 | 2/1991 | Dejter et al. . |
| 5,036,860 | 8/1991 | Leigh et al. . |
| 5,078,142 | 1/1992 | Siczek et al. . |
| 5,111,828 | 5/1992 | Kornberg et al. . |
| 5,127,419 | 7/1992 | Kaldany . |
| 5,133,360 | 7/1992 | Spears . |
| 5,148,813 | 9/1992 | Bucalo . |
| 5,197,484 | 3/1993 | Kornberg et al. . |
| 5,240,011 | 8/1993 | Assa . |
| 5,251,641 | 10/1993 | Xavier . |
| 5,257,632 | 11/1993 | Turkel et al. . |
| 5,271,414 | 12/1993 | Partika et al. . |
| 5,289,520 | 2/1994 | Pellegrino et al. . |
| 5,290,294 | 3/1994 | Cox et al. . |
| 5,353,804 | 10/1994 | Kornberg et al. . |
| 5,415,169 | 5/1995 | Siczek et al. . |
| 5,415,182 | 5/1995 | Chin et al. . |
| 5,419,138 | 5/1995 | Samshide . |
| 5,462,062 | 10/1995 | Rubinstein et al. . |
| 5,472,426 | 12/1995 | Bonati et al. . |
| 5,483,952 | 1/1996 | Arani . |
| 5,488,958 | 2/1996 | Topel et al. . |
| 5,522,398 | 6/1996 | Goldenberg et al. . |
| 5,676,156 | 10/1997 | Yoon ........................................ 600/564 |

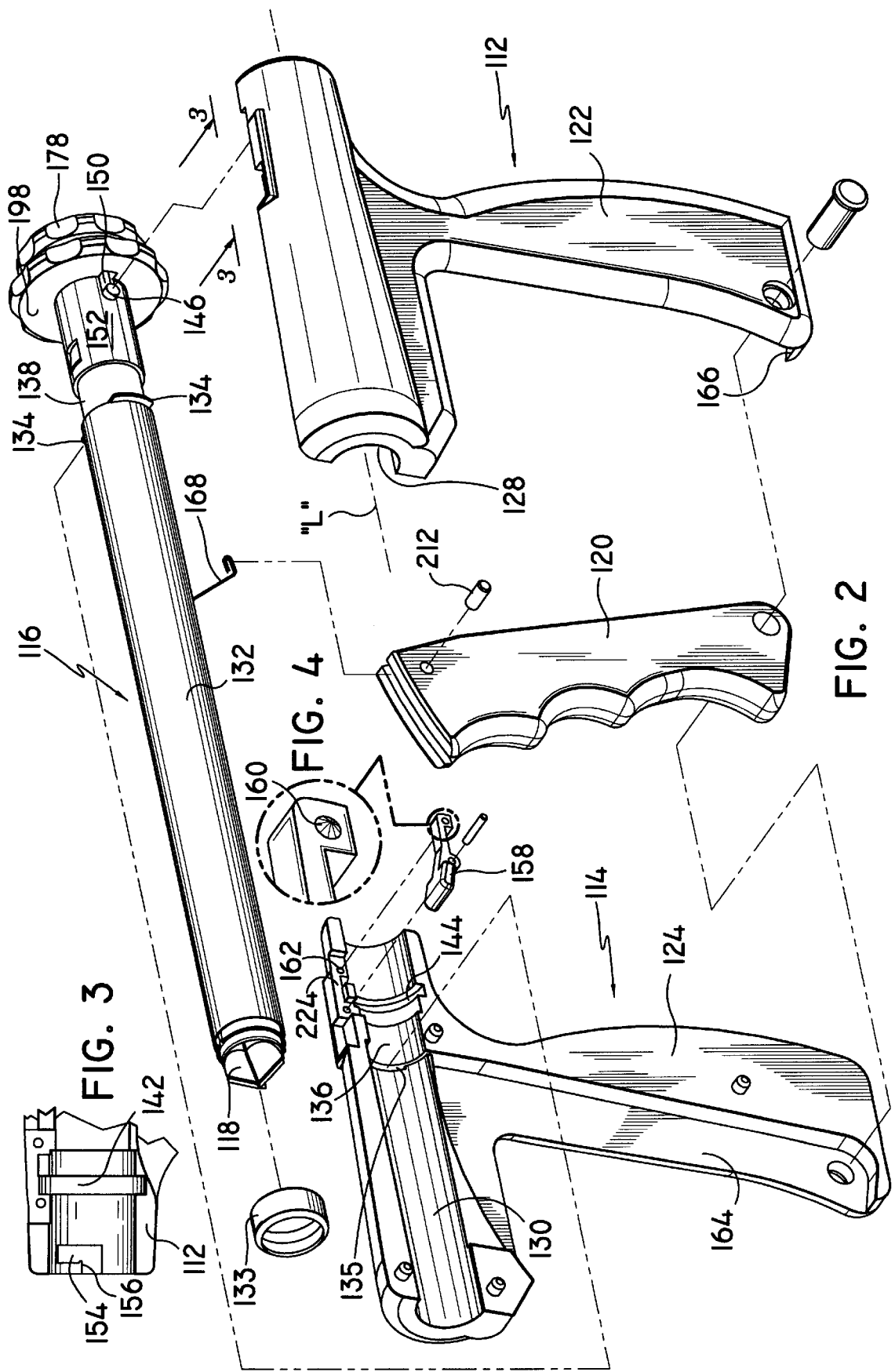

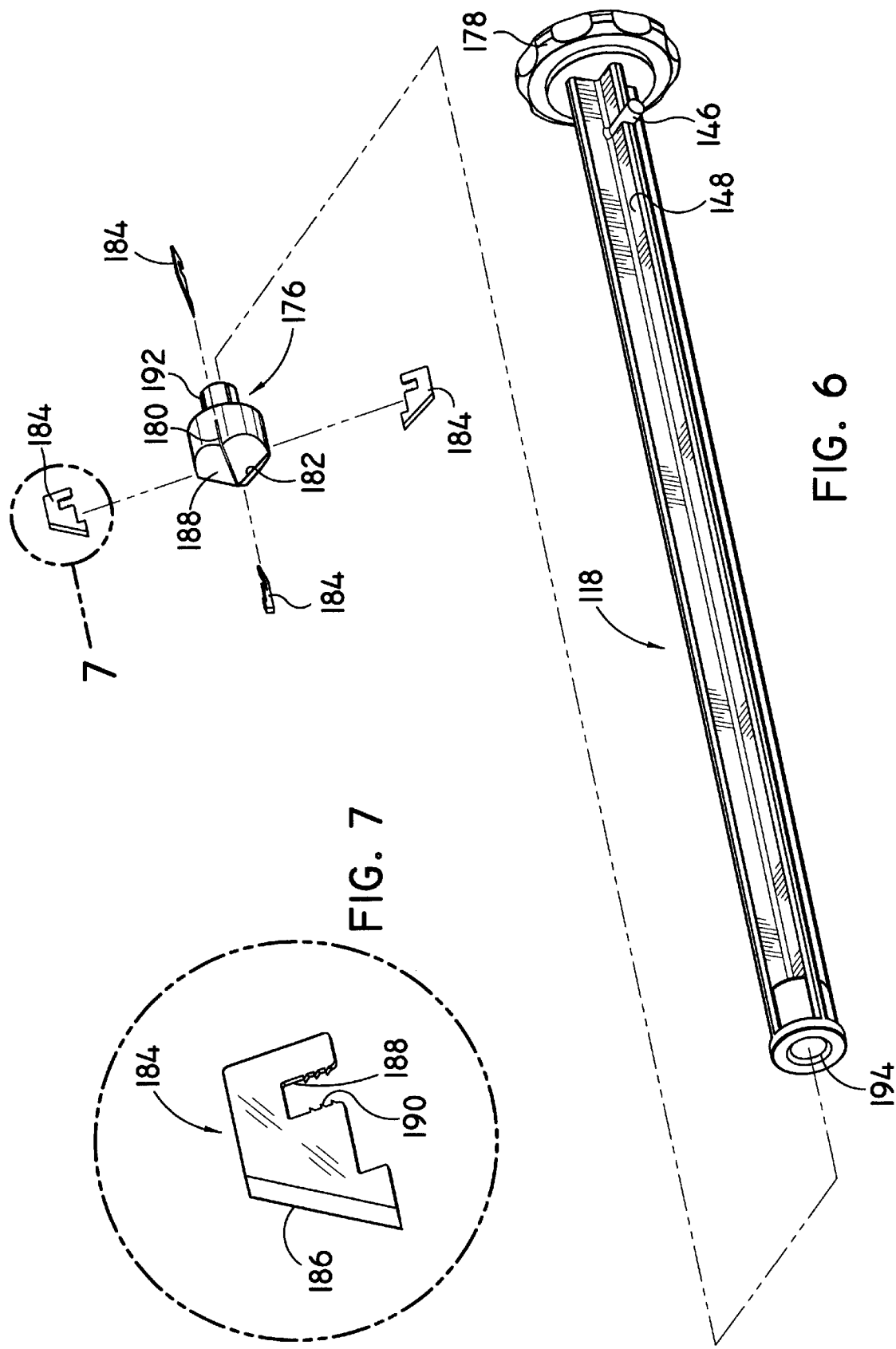

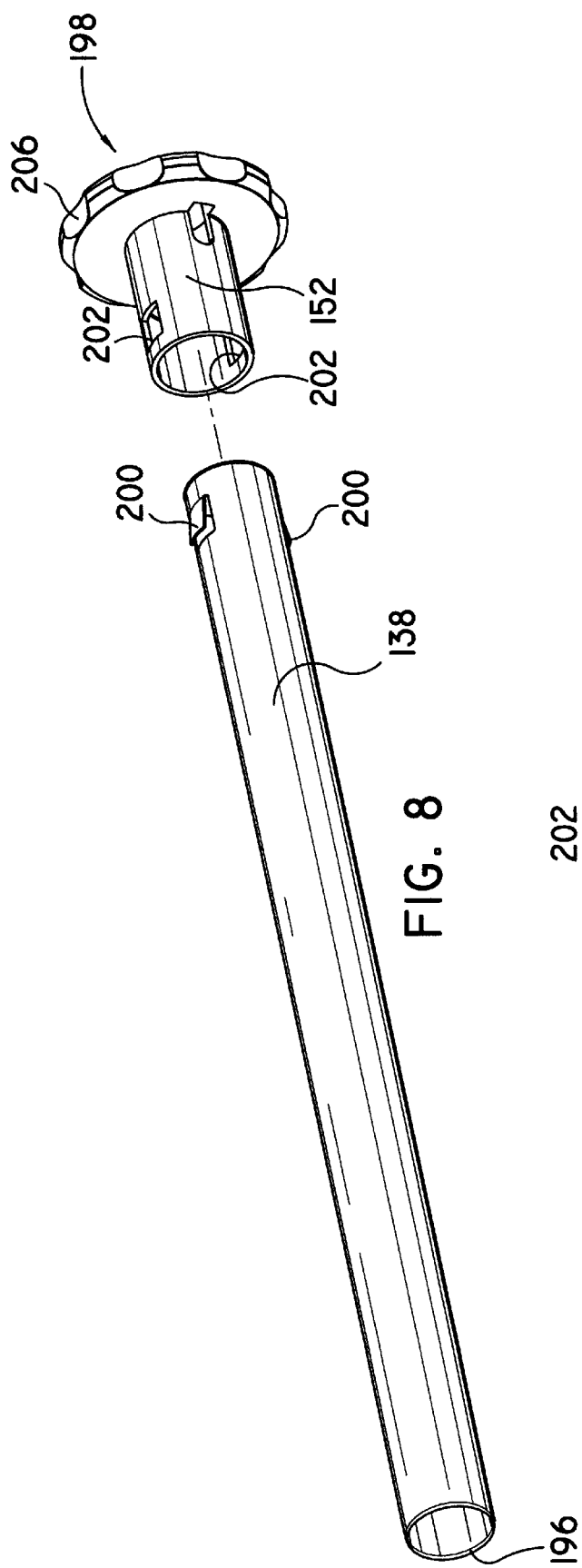
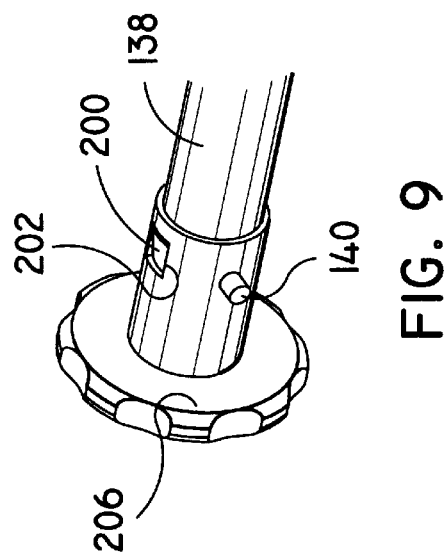

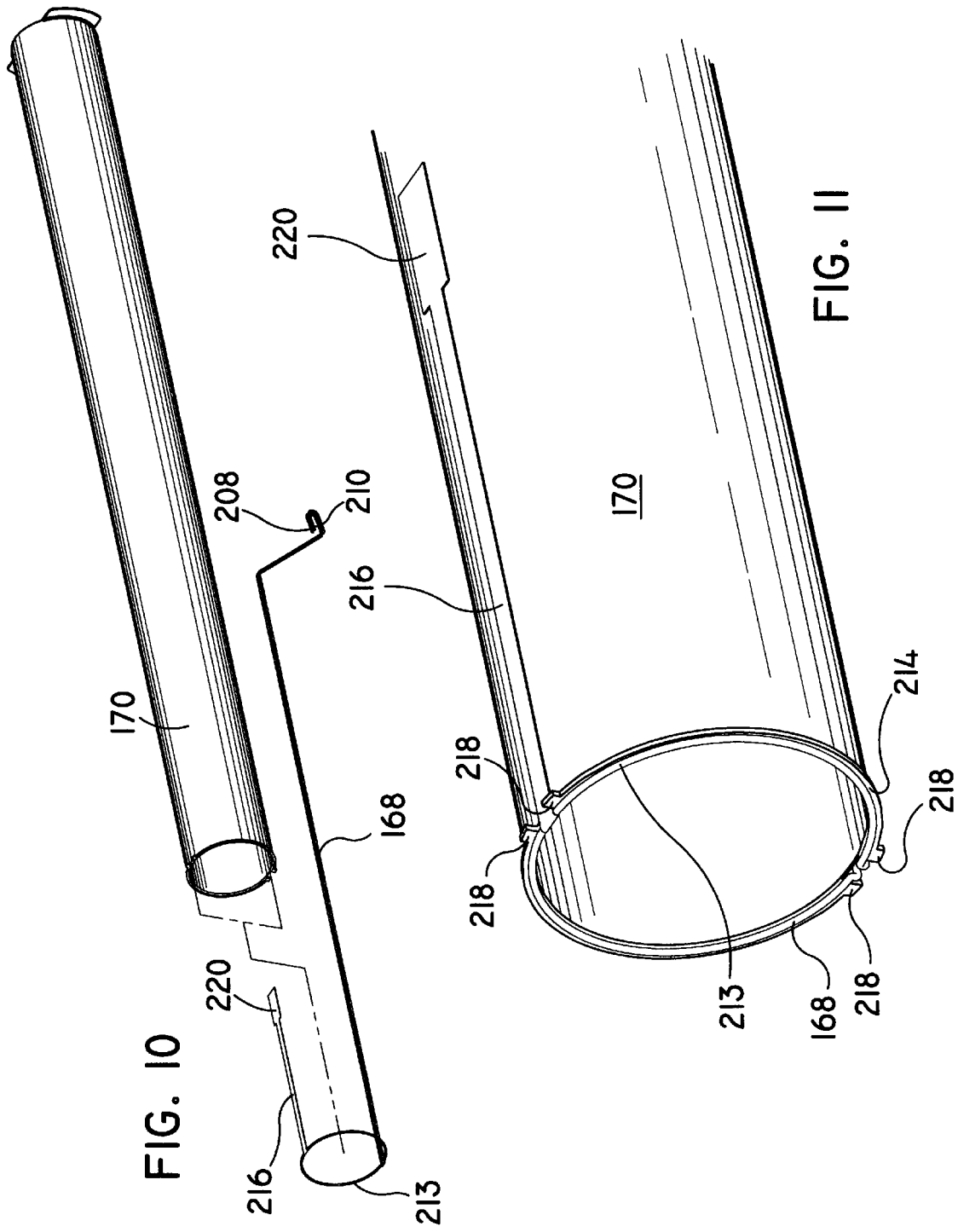

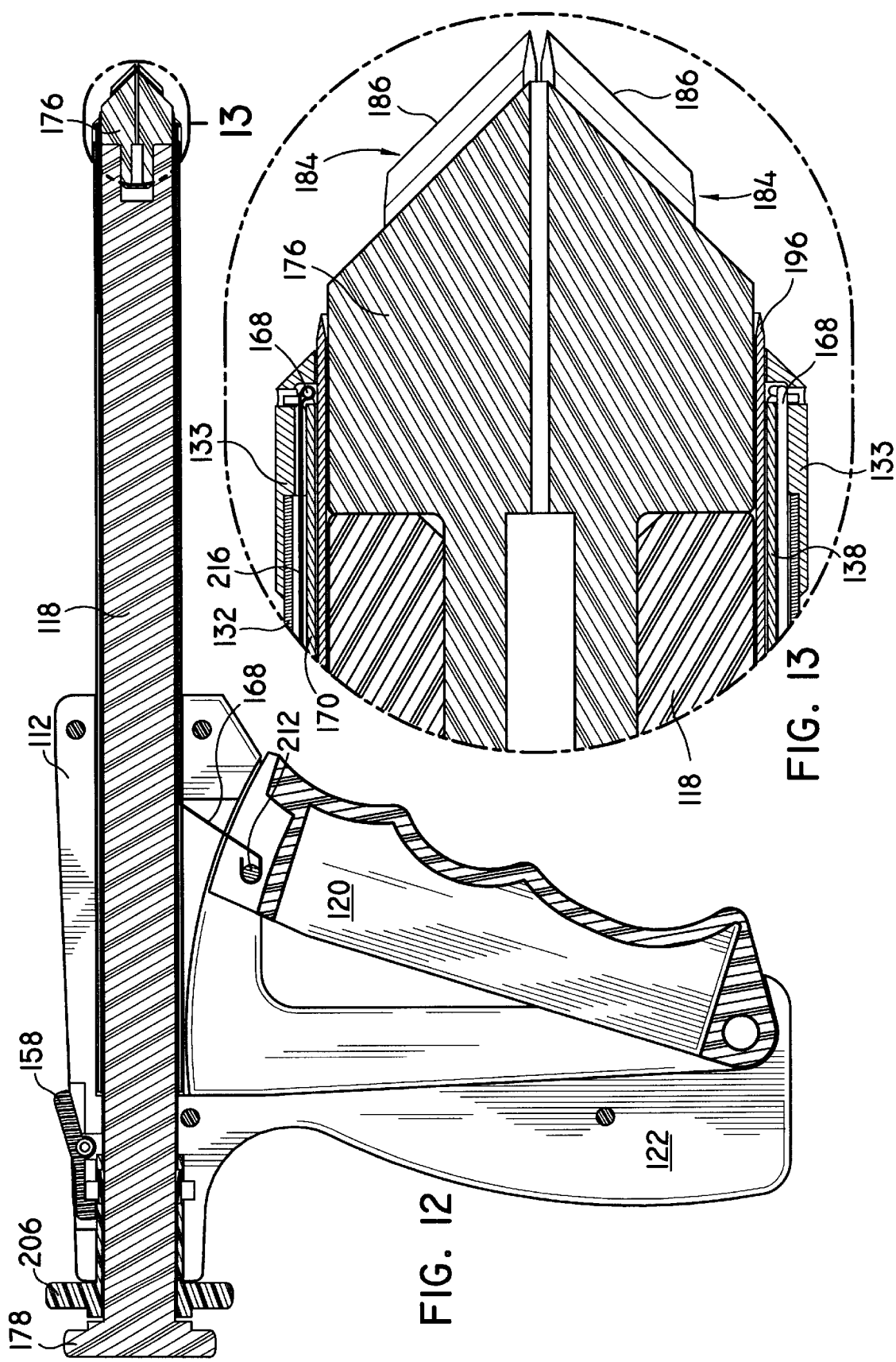

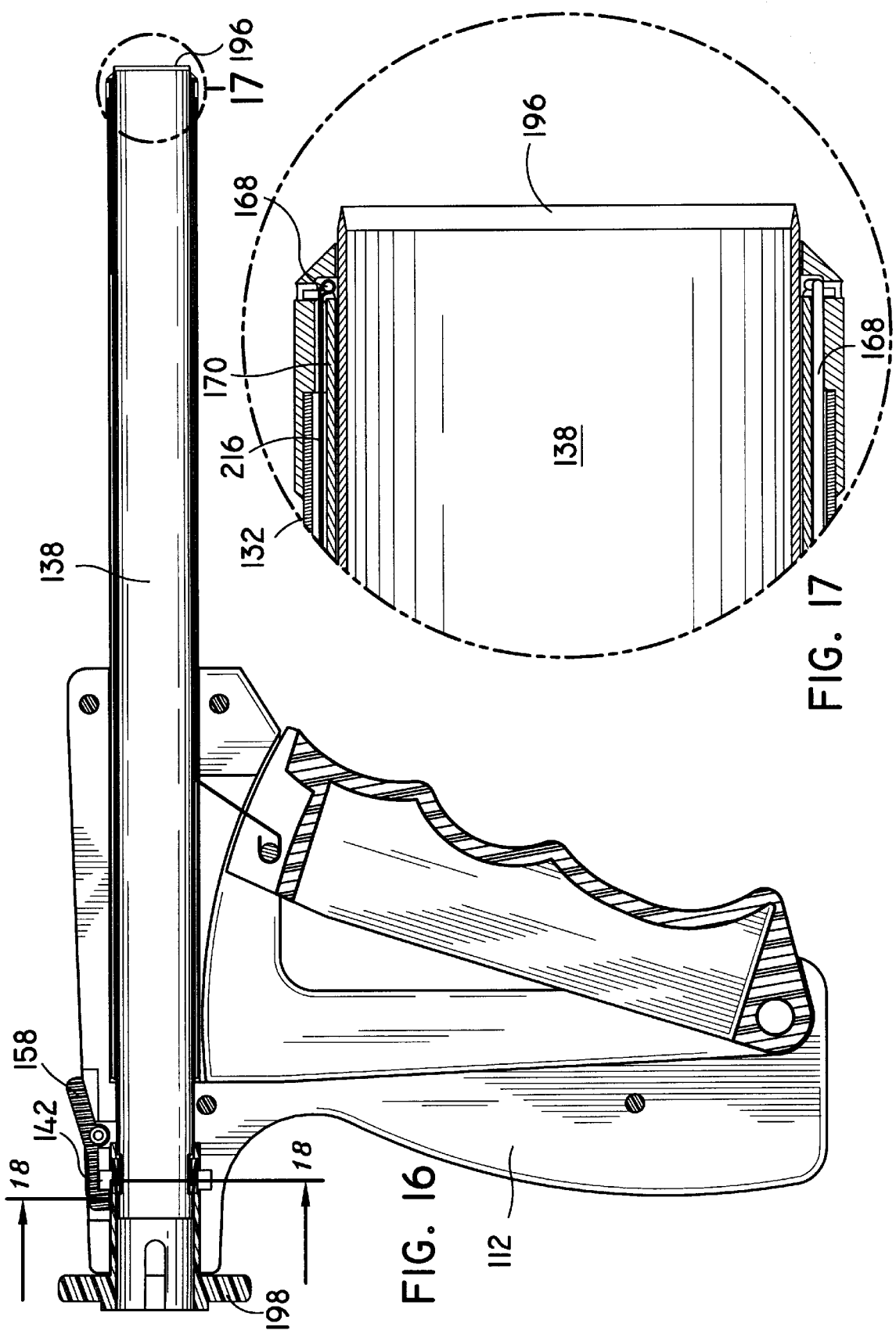

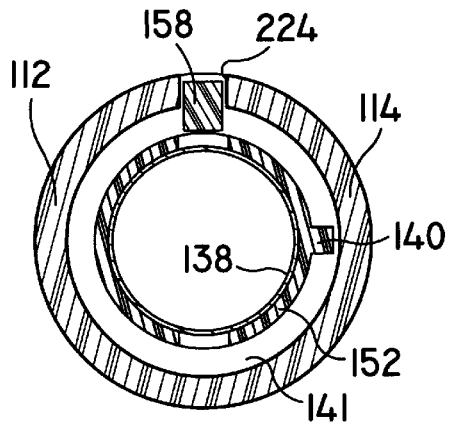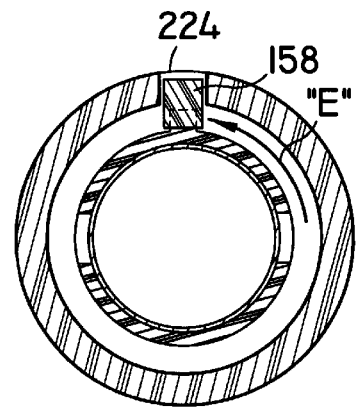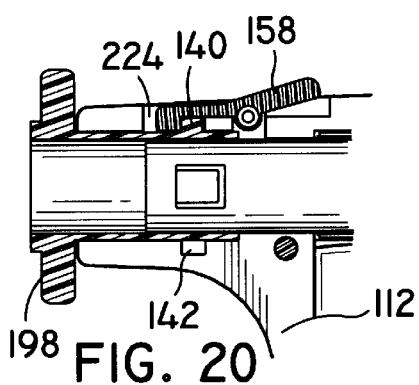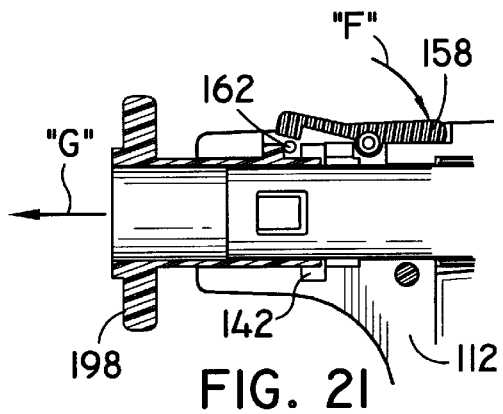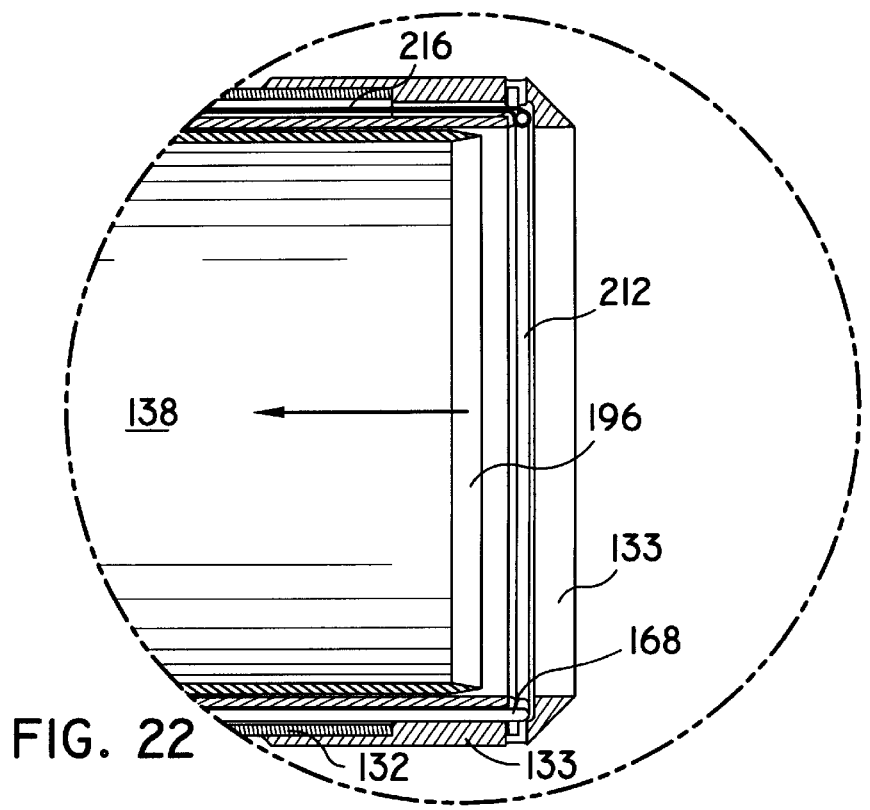

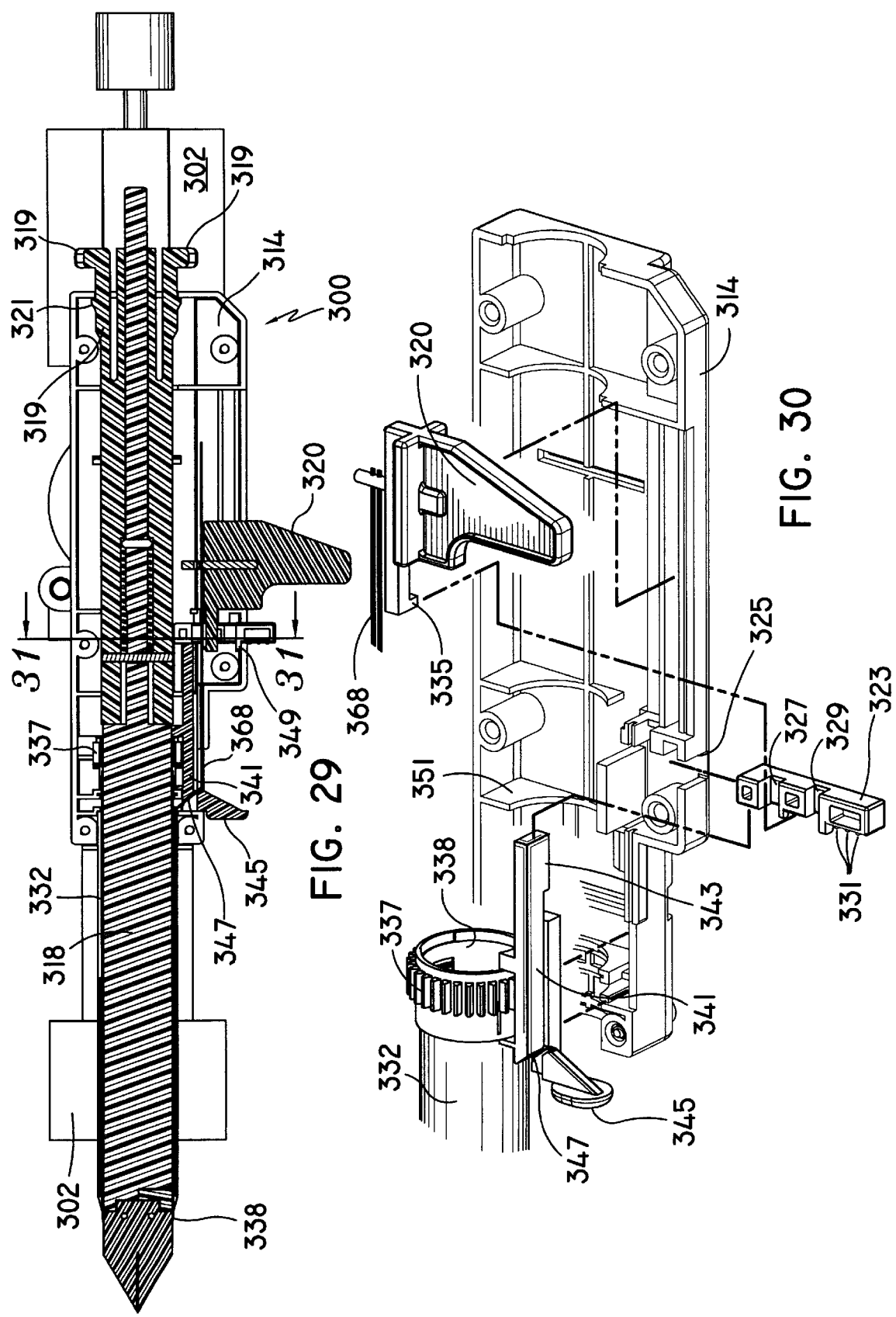

APPARATUS FOR REMOVING TISSUE

CROSS REFERENCE TO RELATED APPLICATION

This application is a continuation of and claims priority to U.S. Application Ser. No. 08/525,450 filed Sep. 8, 1995 by Milliman et al., entitled APPARATUS AND METHOD FOR REMOVING TISSUE, now U.S. Pat. No. 5,857,982.

BACKGROUND

1. Technical Field

The present disclosure relates to apparatus and method for biopsy/removal of tissue from within a patient's body. More particularly, the present disclosure relates to apparatus and method for breast tissue biopsy/removal.

2. Background of Related Art

Numerous surgical instruments have been developed for performing minimally invasive surgical procedures. Such procedures greatly reduce recovery time for the patients in comparison to conventional open surgical procedures. Minimally invasive instruments also reduce damage to tissue surrounding the operative site. The enormous success of such instruments in procedures such as gall bladder removal and hernia repair has led to increased development of minimally invasive instruments for other operative procedures as well.

One area where minimally invasive instruments have been utilized is in performing biopsies of target breast tissue to determine whether the tissue is malignant or benign. As is quite often the case, lesions within the breast are non-palpable, therefore, making cancerous lesions more difficult to diagnose. Early diagnosis of suspect lesions in a patient's breast, however, has been greatly enhanced through the development of imaging machines, for example, stereotactic mammography imaging systems (hereafter referred to as "stereotactic machines"). In such machines, an elongated prone supporting examining table for x-ray mammography is provided with a central breast receiving aperture, through which the patient's pendulant breast is exposed to a horizontal beam of x-rays from a source which is angularly movable through an arc centered on the patient's breast. Thus, x-ray projection through more than 360 degrees around the patient's body is possible. An example of such a stereotactic machine is disclosed in U.S. Pat. No. 5,289,520 which issued on Feb. 22, 1994 to Pellegrino et al., the contents of which are hereby incorporated by reference.

Fine needle biopsy is also facilitated by stereotactic machines. In such procedures, doctors can take advantage of the precision instrument positioning and suspect tissue position locating capabilities of the machine's imaging systems, to precisely insert a biopsy needle and retrieve a tissue sample.

However, minimally invasive instrumentation to efficiently and efficaciously biopsy and/or remove tissue so as to potentially avoid open surgical techniques are not readily available. The present disclosure provides minimally invasive apparatus which are relatively easy to use and inexpensive to reliably manufacture and use. The present disclosure also provides apparatus and method(s) for removing breast tissue using minimally invasive techniques.

SUMMARY

The present disclosure provides a surgical apparatus for removing tissue, which includes a housing, an elongated body which extends from the housing and forms an opening at a distal end, the elongated body further forming a tissue receiving cavity in communication with the opening, a cutting member operatively associated with the housing and configured to cut tissue in proximity to the opening in a direction transverse to the elongated body, and a tissue retaining member positioned in proximity to the opening and the cutting member, the retaining member being selectively movable from a retracted position to a deployed position, wherein when positioned in the deployed position, the tissue retaining member obstructs at least a portion of the opening at the distal end of the elongated body.

Preferably, the tissue retaining member is operatively connected to the cutting member such that movement of the cutting member across (or transverse to) the elongated body causes movement of the tissue retaining member from the retracted position to the deployed position. In one embodiment, the tissue retaining member is a strap. Also, in one embodiment, the cutting member is a filament and preferably a wire. The cutting member may also be adapted to cooperate with a source of electrocautery current (e.g., by way of a conventional cautery adapter on the housing) so as to cauterize tissue while making a cut therethrough.

In another embodiment of the present disclosure a surgical apparatus for removing tissue is provided which includes an elongated body defining an opening at a distal end, the elongated body further forming a tissue receiving cavity in communication with the opening, a tubular member movable relative to the elongated body, the tubular member having a tissue cutting surface formed at a distal end thereof, and a tissue cutting member disposed adjacent the tubular member, at least a portion of the tissue cutting member being movable in a direction transverse to the elongated body in proximity to the opening, the tissue cutting member and the tubular member being movable independently of each other.

The tubular member is preferably rotatably movable relative to the housing and longitudinally movable relative to the housing.

Additionally, a locking mechanism to prevent longitudinal movement of the tubular member and a penetrating member having a sharpened distal end portion may be provided.

As a further feature, a lockout disposed on the housing may be provided which, when engaged, interacts with a portion of the penetrating member to prevent rotation of the penetrating member with respect to the housing. The tubular member is preferably adapted to interact with the lockout and the portion of the penetrating member to prevent rotation of the tubular member when the lockout is engaged.

The penetrating member may be removable from the housing and may interact with a lockout disposed on the housing which, when engaged, prevents removal of the penetrating member from the housing.

A further embodiment of the present disclosure provides a surgical apparatus for removing tissue which includes an elongated body defining an opening at a distal end, the elongated body further forming a tissue receiving cavity in communication with the opening, a tubular member movable relative to the elongated body, the tubular member having a tissue cutting surface formed at a distal end thereof, a tissue cutting member disposed adjacent the tubular member, at least a portion of the tissue cutting member being movable in a direction transverse to the elongated body in proximity to the opening, the tissue cutting member and the tubular member being movable independently of each other, and an actuator operatively connected to the tissue cutting member, wherein the at least a portion of the tissue cutting member is moved transverse to the elongated body upon movement of the actuator from a first position to a second position.

An additional feature of this embodiment is a safety lockout movable from at least a first position wherein the actuator is prevented from moving, to a second position wherein the actuator is movable relative to the housing. This embodiment may also include a penetrating member removably disposed within the housing, the penetrating member having a sharpened distal end portion. With the penetrating member positioned in the housing, the lockout is prevented from moving to the second position.

Additionally, a safety lockout may be included which is movable from at least a first position wherein the tubular member is prevented from moving, to a second position wherein the tubular member is not prevented from moving. Alternatively, the safety lockout may be positionable in a first position wherein both the tubular member and the actuator are prevented from moving, a second position wherein the tubular member is movable and the actuator is prevented from moving, and a third position wherein the tubular member is prevented from moving and the actuator is movable relative to the housing to permit the user to effect cutting with the cutting member.

The lockout may be prevented from moving to at least one of the second or third positions when a penetrating member is positioned within the housing.

As an additional feature, a control member may be provided which is operatively associated with the tubular member to facilitate longitudinal movement of the tubular member relative to the housing. A safety lockout may be operatively associated with the control member and movable from at least a first position wherein the control member is prevented from moving to a second position wherein the control member is movable relative to the housing.

The present disclosure also provides a method for surgically removing tissue which includes the steps of positioning a tissue removing instrument including an elongated housing having a tissue receiving cavity at a distal end, a first tissue cutting surface longitudinally movable relative to the elongated housing distal end, an obturator having a tissue-contacting distal end portion such that the tissue-contacting end portion is positioned adjacent the tissue to be removed and a tissue cutting surface transversely movable relative to the elongated housing, removing the obturator from the elongated housing, coring the tissue to be removed, severing the cored tissue from the surrounding tissue with the cutting surface, and removing the severed tissue from the patient.

BRIEF DESCRIPTION OF THE DRAWINGS

Various embodiments are described herein with reference to the drawings, wherein:

FIG. 2 is a perspective view with parts separated, of the embodiment of FIG. 1;

FIG. 3 is a partial view of the interior distal end of one handle half-section of the embodiment of FIG. 1;

FIG. 4 is an enlarged view of the area of detail indicated in FIG. 2;

FIG. 6 is a perspective view, with parts separated, of the obturator of the embodiment of FIG. 1;

FIG. 7 is an enlarged view of the area of detail indicated in FIG. 6;

FIG. 8 is a perspective view, with parts separated, of the elongated tissue coring tube of the embodiment of FIG. 1;

FIG. 9 is a perspective view of the tissue coring tube of FIG. 8, which shows the reverse side of the distal end of the tube;

FIG. 10 is a perspective view, with parts separated, of the cutting wire and support tube of the embodiment of FIG. 1;

FIG. 11 is an enlarged perspective view of the distal end of the cutting wire positioned on the support tube;

FIG. 12 is a horizontal cross-sectional view of the embodiment of FIG. 1;

FIG. 13 is an enlarged view of the indicated area of detail of the distal end of the instrument shown in FIG. 12;

FIG. 16 is a horizontal cross-sectional view of the embodiment FIG. 1 with the obturator removed therefrom;

FIG. 17 is an enlarged view of the area of detail indicated in FIG. 16;

FIG. 18 is a cross-sectional view taken along section line 18—18 of FIG. 16;

FIG. 19 is a view, similar to FIG. 18, showing operational features of the instrument;

FIG. 20 is a cross-sectional view of the proximal end of the embodiment of FIG. 1, showing the lockout lever in the locked position;

FIG. 21 is a view, similar to FIG. 20, showing the lockout lever in the released position;

FIG. 22 is a view, similar to FIG. 17, showing the movement of the central elongated tube;

FIG. 29 is a longitudinal cross-sectional view from the top of the embodiment of FIG. 28;

FIG. 30 is a perspective view, with parts separated, of the components contained in the housing or handle portion of the embodiment of FIG. 28;

DETAILED DESCRIPTION OF PREFERRED EMBODIMENTS

Figure 1:
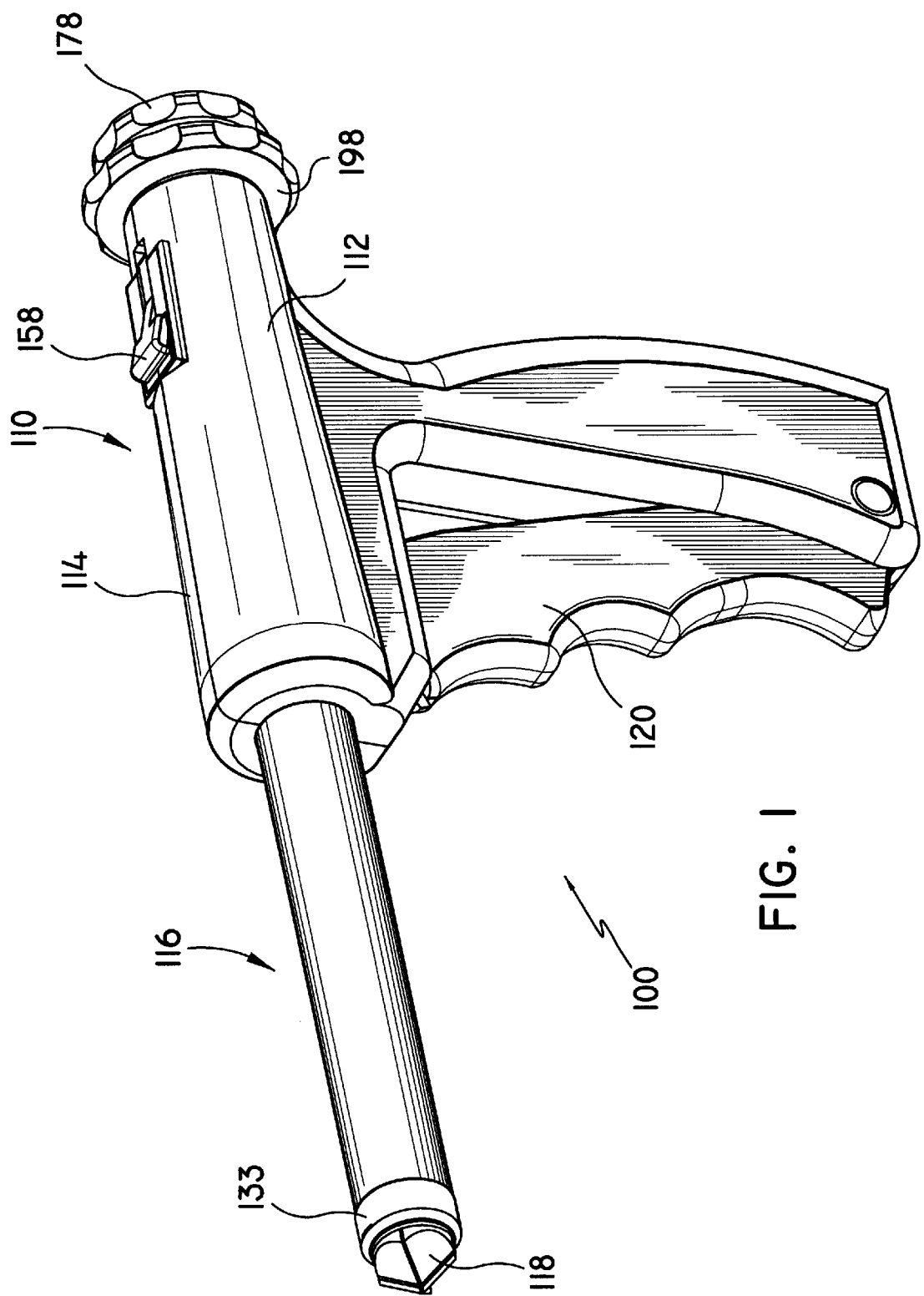
FIG. 1 is a perspective view of one embodiment of a tissue removing instrument constructed in accordance with the present disclosure.

Referring initially to FIGS. 1–5, one embodiment of an instrument for removing and/or taking a biopsy of tissue in accordance with the present disclosure is designated by reference numeral 100 throughout the several views. The instrument 100 is particularly adapted for minimally invasive insertion into tissue immediately adjacent the target tissue, and then for coring out and removing the target tissue from the patient. It will be understood by those skilled in the art, however, that the embodiments of the tissue removing instrument described herein, although generally directed to removal of breast tissue, may also be utilized for removal and/or biopsy of target tissue from other areas of a patient's body as well.

Generally, instrument 100 includes a housing such as body portion 110 (formed from handle half-sections 112 and 114), and an elongated tubular body portion 116. A penetrating member, such as obturator 118 extends through a longitudinal passageway of instrument 100 and extends out the distal end. An actuator, for example trigger 120 is preferably pivotally mounted in an opening formed between handle halfsections 112 and 114. Except where noted otherwise, the materials utilized in the components of the instrument generally include such materials as polycarbonate for housing sections and related components, and stainless steel for components which transmit forces. One preferred polycarbonate material is available from General Electric under the tradename LEXAN. It is also preferred that radiolucent materials be utilized for appropriate instrument components, e.g., elongated tubular portions, so as not to interfere with imaging of tissue positioned adjacent thereto.

The relative assembly of the various structural components of instrument 100 can be readily appreciated with reference to FIGS. 2–13. Referring initially to FIGS. 1 and 2, handle half-sections 112 and 114 are preferably molded to have predetermined contoured regions for housing the various components as well as facilitating the instrument's operation. Each of the handle half-sections 112 and 114 has a grip portion 122, in the shape of a pistol grip, which extends generally transversely away from a longitudinal axis "L" of a barrel portion formed when handle half-sections 112 and 114 are joined. Opposed semi-cylindrical walls 128 and 130 form a generally cylindrical passageway with adjacent semi-cylindrical portions, i.e., raised wall portion 136 and semi-annular groove 144, from the proximal end of body 110 to the distal end thereof. Handle half-sections 112 and 114 may be joined together by any suitable means, for example, by sonic welding, snap fit, securing screw(s), adhesive bonding or the like.

Figure 5:
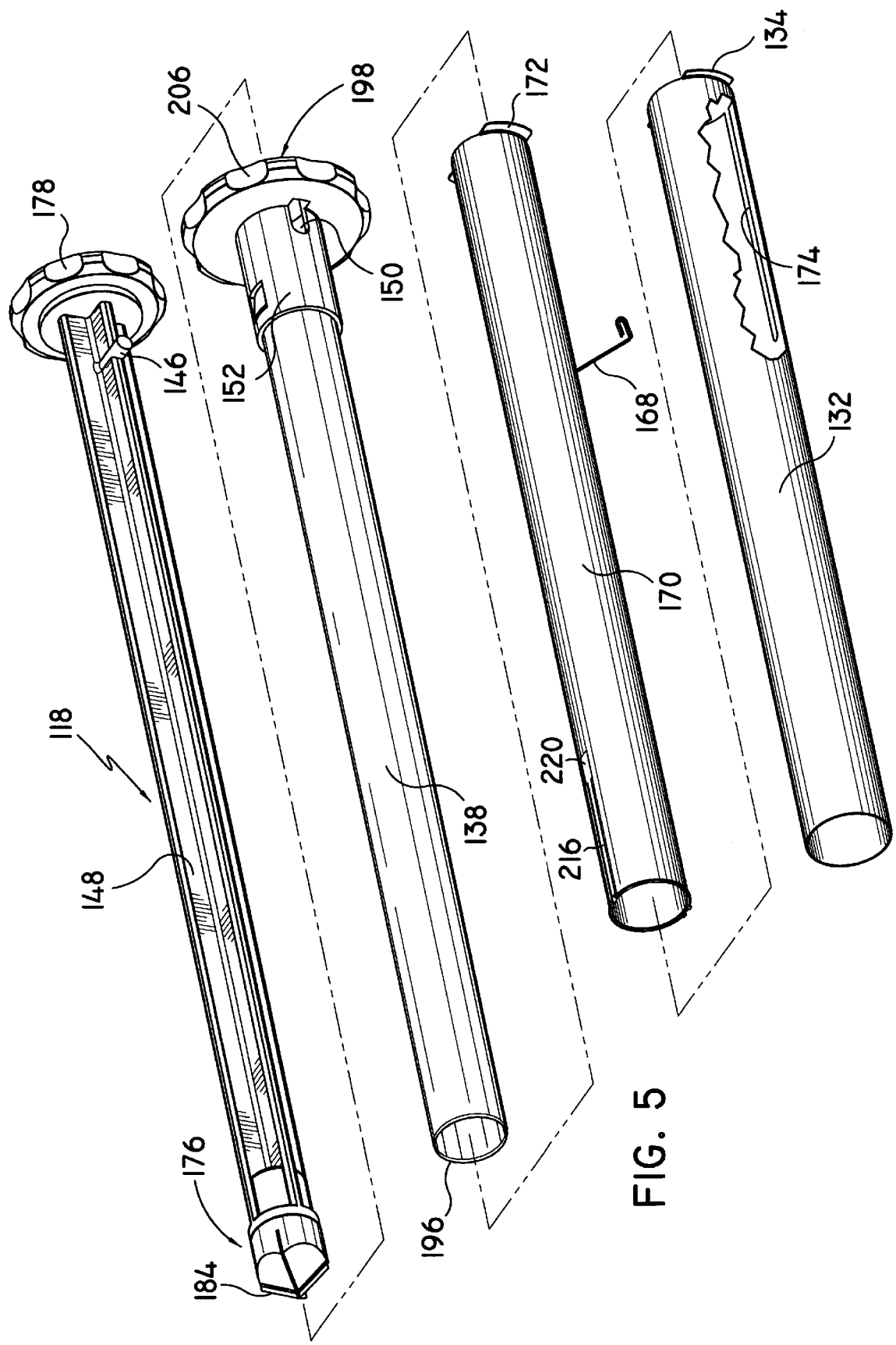
FIG. 5 is a perspective view, with parts separated, of the concentrically disposed tool mechanisms of the embodiment of FIG. 1.

Referring to FIGS. 4 and 5 in conjunction with FIGS. 1 and 2, elongated tubular portion 116 includes a series of elongated components which are preferably concentrically disposed with respect to each other. An outer tubular sheath 132 has a proximal end held securely between semi-cylindrical walls 128 and 130 and a distal end which is covered by a collar 133 securely attached thereto. A pair of transversely extending tab portions 134 are formed at the proximal end of outer tubular sheath 132 and fit into slots 135 formed at the juncture of semi-cylindrical walls 128, 130 and raised portions 135. Tab portions 134 bias against raised portions 136 to prevent proximal movement of outer tubular sheath 132 when the instrument 100 is inserted into the body tissue.

A tubular member, such as central tubular shaft 138, is axially and rotatably movable within outer tubular sheath 132. The rotation of central tubular shaft 138, however, may be selectively prevented by a mechanism described in detail below. Additionally, central tubular shaft 138 may be temporarily and selectively maintained in a fixed axial position relative to barrel portion 126 of body 110. This fixed axial relationship may be accomplished, for example, by a cylindrical protrusion 140 (FIG. 9) formed near the proximal end of central tubular shaft 138 being positioned in an annular groove formed by closing semi-annular groove portions 142 and 144 formed in handle half-sections 112 and 114, respectively. In this manner, central tubular shaft 138 may remain fixed axially within body 110 so as to freely rotate therein but not be removed therefrom.

Obturator 118 is slidably positioned within central tubular shaft 138 and is preferably designed to cooperate with central tubular shaft 138 so as to prevent rotation of both central tubular shaft 138 and obturator 118 during the initial insertion of instrument 100 into the patient. A preferred manner in which to accomplish this selective fixing of the rotational movement of both central tubular shaft 138 and obturator 118 as well as to prevent relative axial movement of those components with respect to each other as well as body 110 is best shown in FIGS. 2, 3 and 5.

In particular, a pin 146 is transversely secured in elongated shaft 148 of obturator 118 near its proximal end. Upon insertion of obturator 118 in central tubular shaft 138, pin 146 is received in a slot 150 formed in a collar 152, which is secured to the proximal end of central tubular shaft 138. This relationship between obturator 118 and central tubular shaft 138 prevents relative rotational movement between the two components. To prevent relative rotational movement between either obturator 118 or central tubular shaft 138 and body 110, the subassembly of obturator 118 and central tubular shaft 138 is secured in body 110 by a bayonet-type mount, FIG. 3, created by the interaction of pin 146 and a lockout groove, such as L-shaped groove 154 formed along the inner wall of handle half-section 112. L-shaped groove 154 is preferably provided with a lip 156 which serves to maintain pin 146 in the locked-out position.

Referring once again to FIGS. 2 and 4, another locking mechanism is shown provided on instrument 100 to facilitate selective axial movement of central tubular shaft 138 once the instrument is inserted around the target tissue. Lockout lever 158 is pivotably mounted to body 110 and is temporarily maintained in the locked-out position by raised portions 160 extending laterally from the side surfaces of lockout lever 158 near a proximal end thereof being seated in detents 162 formed along the inner surface of handle portions of 112 and 114, respectively, at a position proximal of the groove formed by semi-annular groove portions 142 and 144. The operational aspects of lever lockout 158 will be explained in further detail herein.

Trigger 120 is preferably pivotably attached to body 110 in recessed portions 164 and 166 formed in the handle half-sections 112 and 114. Trigger 120 is connected to a tissue cutting member, e.g., a filament or wire, such as wire 168, by a pin extending through a throughbore formed near the top of trigger 120 (FIG. 16). Wire 168 is maintained in a preferred orientation by an elongated tubular sheath 170 which is preferably concentrically disposed within outer tubular sheath 132 such that laterally extending tab portions 172 are situated adjacent tab portions 134 and maintained between housing handle half-sections 112 and 114 as described above for outer tubular sheath 132. A longitudinal slot 174 is formed beginning at the proximal end of outer tubular sheath 132 and is disposed between laterally extending tab portions 134 so as to receive wire 168 and permit movement of the wire loop with respect to outer tubular sheath 132.

Referring now to FIGS. 6–13, the various structural subassemblies will now be described individually. As shown in FIGS. 6 and 7, obturator 118 includes elongated shaft 148, a cutting head 176 secured to a distal end of the shaft and a knob 178 attached to a proximal end of the shaft to facilitate insertion and removal of the obturator 118 from the instrument 100. Cutting head 176 is preferably provided with slots 180 and 182, formed orthogonally with respect to each other and which are dimensioned to receive individual blades 184 such that a cutting edge 186 formed on each blade 184 is angled to correspond to the angled distal surfaces 188 of the cutting head 176.

To facilitate assembly of the cutting head 176, individual blades 134 are each provided with a transversely extending slot 188 having a series of individual tooth members 190 extending from the side wall of the slot. Teeth 190 are preferably formed in the shape of a ramp-shaped canuning surface to interlock with complimentary surfaces (not shown) formed within orthogonally disposed slots 180 and 182. Cutting head 176 is in the shape of a plug member having a proximally extending portion 192 of reduced diameter which is inserted into a bore 194 formed at the distal end of obturator 118 so as to be fixedly secured thereto. Any suitable known techniques for mounting may be utilized, such as friction fitting, bonding, adhesives or the like.

As shown in FIGS. 8 and 9, central tubular shaft 138 has a tissue cutting surface, such as annular cutting edge 196 formed at the distal end to facilitate coring of the tissue surrounding and including the target tissue within the patient. The shaft is preferably formed of a material suitable for forming a sharpened edge, such as, for example, stainless steel. A knob 198 is secured to the proximal end of central tubular shaft 138, for example, by locking tabs 200 engaging cut out portions 202 formed in cylindrical section 152 of knob 198. Knob 198 is preferably further provided with a knurled gripping surface 206 to facilitate rotation of the shaft during the coring action of the tissue. Such rotational movement is facilitated by the disposition of pin 140 within the annular groove formed by semi-annular groove portions 142 and 144, as noted above.

In FIGS. 10 and 11, the cutting assembly including wire 168 and elongated tubular sheath 170 are shown in detail. As will be described later herein, wire 168 facilitates the severing of the tissue core to permit removal of the targeted tissue from the patient and, optionally, delivers electrocautery current to the tissue as cutting is accomplished. Wire 168 is preferably formed of a single length of thin gauge, stainless steel wire which is bent to an initial configuration or pre-fired condition contained within instrument 100, as shown in FIG. 10.

Initially, wire 168 is folded in half such that free ends 208 and 210 are positioned at the proximal end and are formed into a U-shaped bend to hook around pin 212 disposed at the top of trigger 120 (FIGS. 2 and 17). Wire 168 extends longitudinally along the outer surface of elongated tubular sheath 170 to the distal end thereof. A circular loop 213 is formed at the distal end of wire 168 and is positioned adjacent a flange 214 formed at the distal end of the tubular sheath 170. Flange 214 is provided with radially extending leg portions 218 which form diametrically opposed passageways which hold wire 168 in a position substantially aligned with the distal end of tubular sheath 170. A tissue retaining member, such as strap 216, is wrapped around circular loop 213 and is provided with a tabbed end portion 220 to maintain the positioning of the strap across the distal opening of elongated tubular sheath upon cutting of the tissue core, which will explained in greater detail herein.

The relative positioning of the various structural subassemblies in the initial configuration of instrument 100 is shown in the longitudinal cross-sectional view of FIG. 12. In particular, obturator 118 is shown inserted in instrument 100 with lockout lever 158 preventing proximal movement of central tubular shaft 138. As best seen in the greatly enlarged view of FIG. 13, wire 168 is maintained in position by central tubular shaft 138 and obturator 118 on the interior side and by collar 133 on the exterior side. Wire 168 cannot be deployed to cut tissue until both obturator 118 and central tubular shaft 138 are moved distally of loop 213 (FIG. 10).

A preferred method of using instrument 100 is illustrated in FIGS. 14–27. Instrument 100 is inserted into the breast tissue along a predetermined path toward the target tissue 222. The location of the target tissue can be specifically determined through the use of known localization techniques, such as for example, the insertion of a localization needle and/or the use of a stereotactic mammography device. Thus, for example, the target tissue may be tagged with a tagging device and instrument 100 moved adjacent the tagged location under conventional imaging guidance, or instrument 100 may be adapted to move along a target tissue locating device, such as a conventional K-wire, which was pre-positioned adjacent or across the target tissue. Instrument 100 may cooperate with a target tissue locating device in a variety of manners such as sliding coaxially along such locating device.

Figure 14:
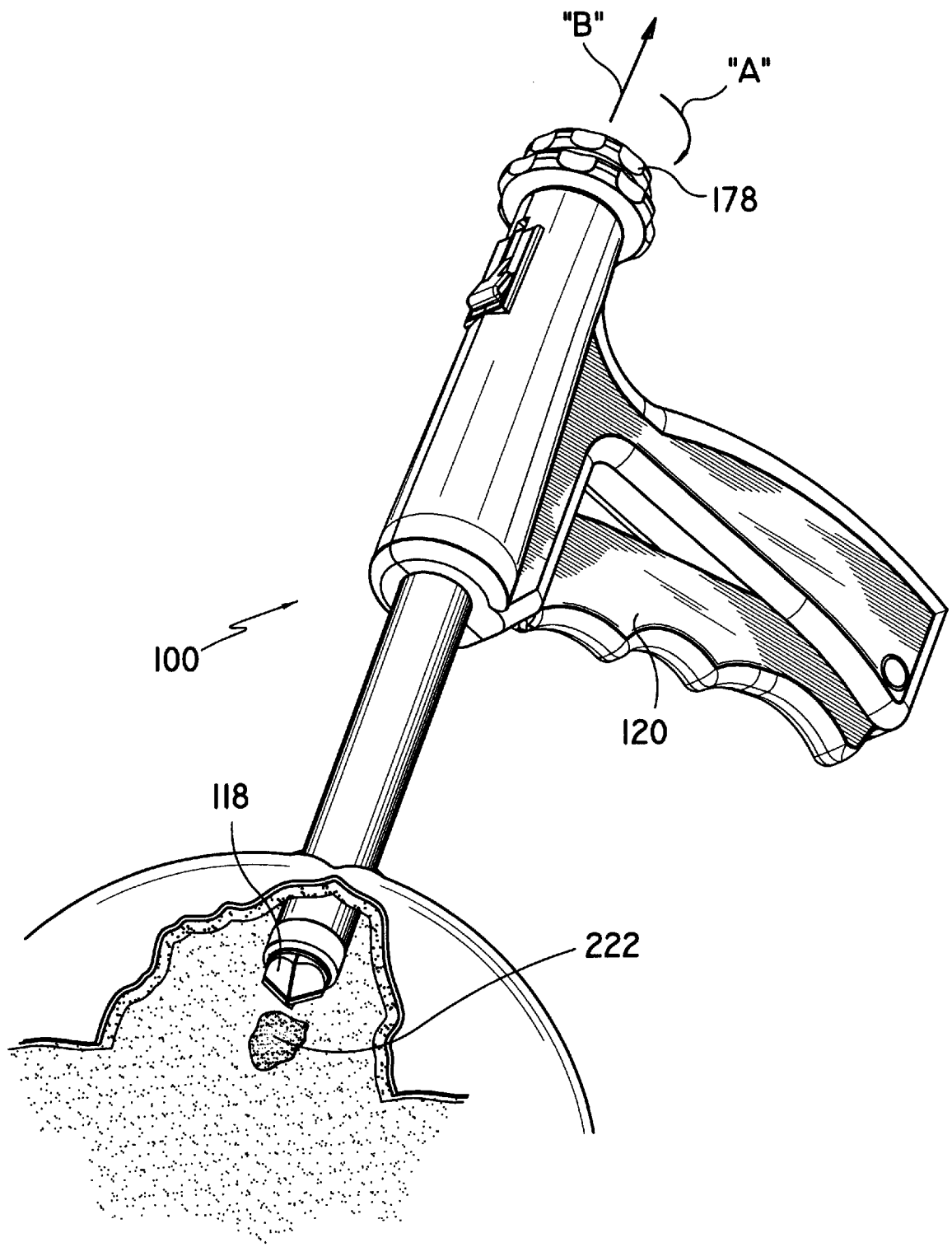
FIG. 14 is an initial view showing the embodiment of FIG. 1 in use.

Once instrument 100 is inserted to a position immediately adjacent the target tissue, obturator 118 is first rotated in a counterclockwise fashion as indicated by arrow "A" in FIG. 14, by the user gripping knob 178 and rotating the knob in a counterclockwise fashion. This rotational movement disengages pin 146 from L-shaped groove 154 (FIGS. 3 and 6) to permit axial movement of obturator 118 relative to the instrument 100. In particular, obturator 118 may be removed from the instrument 100 by pulling on knob 178 in a proximal direction as indicated by arrow "B" in FIG. 14.

Figure 15:
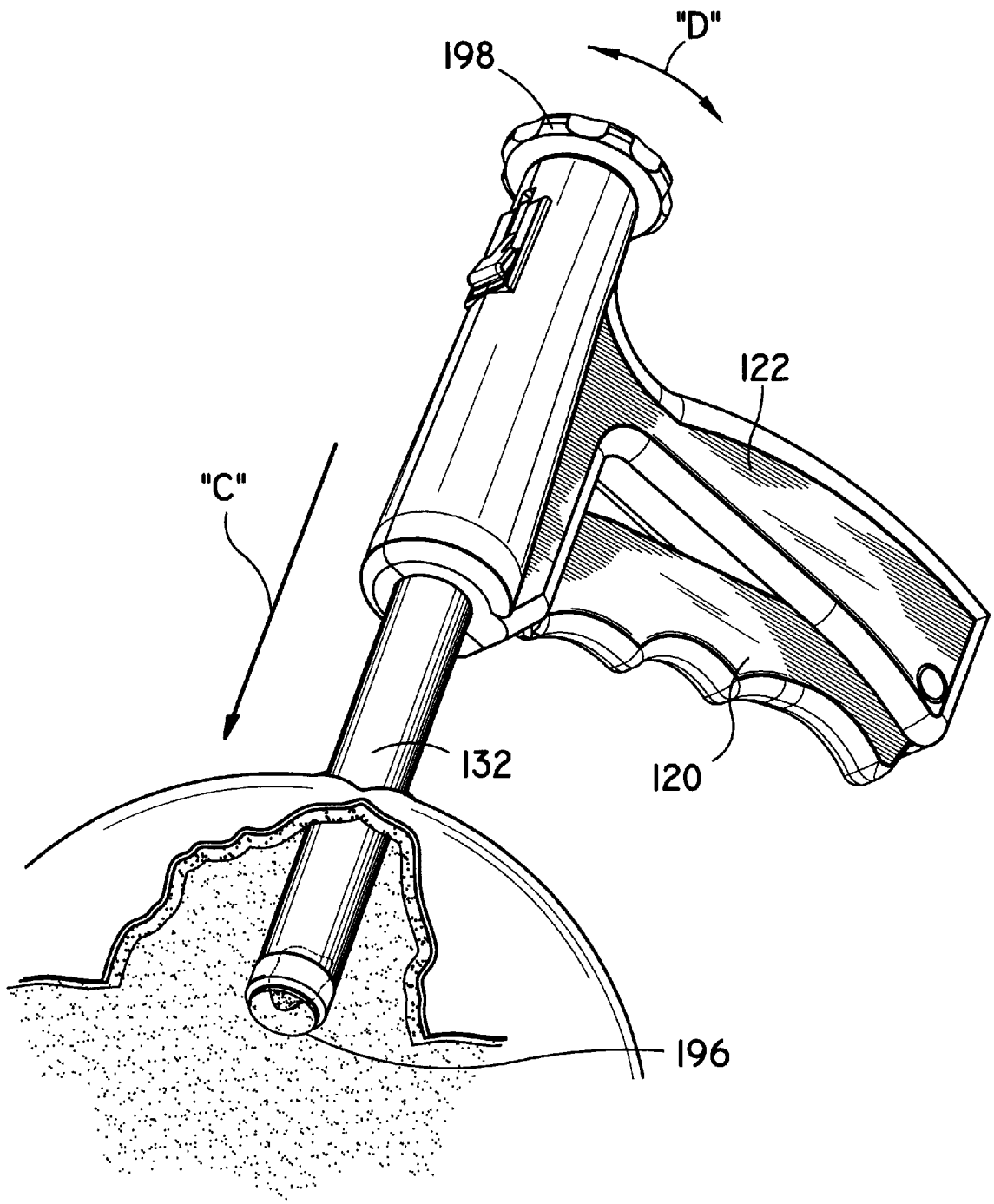
FIG. 15 is a further view, similar to FIG. 14, showing the embodiment of FIG. 1 in use.
Figure 23:
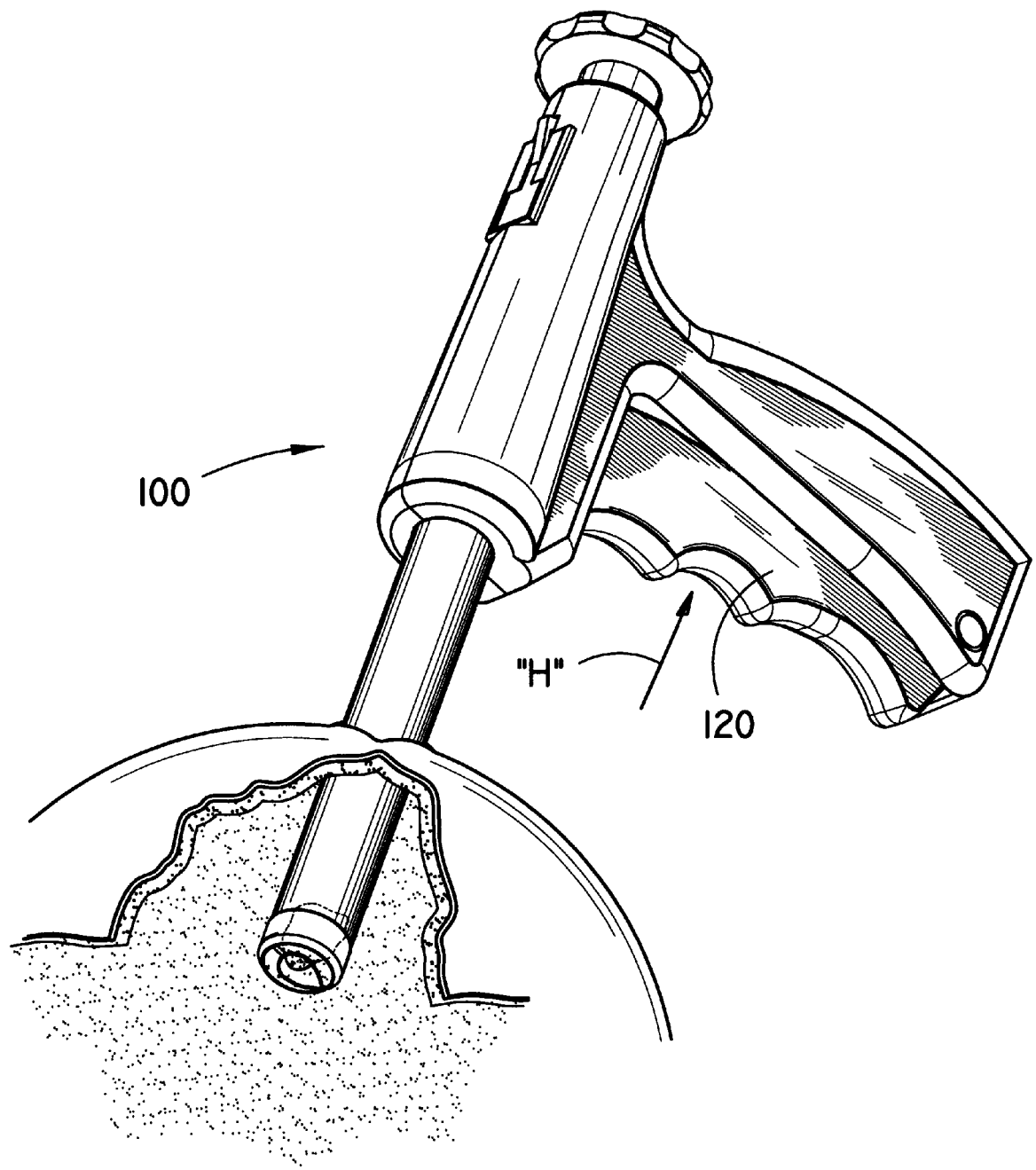
FIG. 23 is a further view, similar to FIG. 14, showing the embodiment of FIG. 1 in use.

With the obturator 118 removed, the target tissue is cored out from the surrounding tissue by urging instrument 100 in a proximal direction as indicated by arrow "C" in FIG. 15, while simultaneously turning knob 198 of central tubular shaft 138 to cause rotation of annular cutting edge 196 at the distal end of the central tubular shaft 138. Rotation of the elongated central tubular shaft 138 may be in either a clockwise or counterclockwise direction or both depending on the preference of the user, as indicated by arrow "D" in FIG. 15.

When the target tissue is completely within the distal end of instrument 100, central tubular shaft 138 is moved proximally to allow for deployment of wire loop 168 to sever the tissue core from the patient. Electrocautery current is optionally delivered to the tissue by wire loop 168 as severing is accomplished. As shown in FIGS. 16 and 17, elongated central tubular shaft 138 is shown extending distally from the distal end of instrument 100 and preventing wire loop 168 from moving out of alignment with the circumferential alignment with the distal end of elongated tubular sheath 170.

FIG. 18 shows the relative positioning of pin 140 within annular groove 141 to facilitate the rotation of elongated central tubular shaft 138 therein. Such rotation is possible when the obturator 118 is removed from instrument 100. When the tissue core is of sufficient depth, knob 198 is rotated, as indicated by arrow "E" in FIG. 19, to align pin 140 with a keyway 224 formed in handle half-sections 112 and 114. This alignment permits proximal movement of central tubular shaft 138 when lever lockout 158 is pushed down, as indicated by arrow "F" in FIG. 21, to release protrusion 160 from detent 162 (FIGS. 2 and 4). Knob 198 is pulled proximally as indicated by arrow "G" in FIG. 21 to move the distal end of central tubular shaft 138 proximal of wire loop 213.

Figure 25:
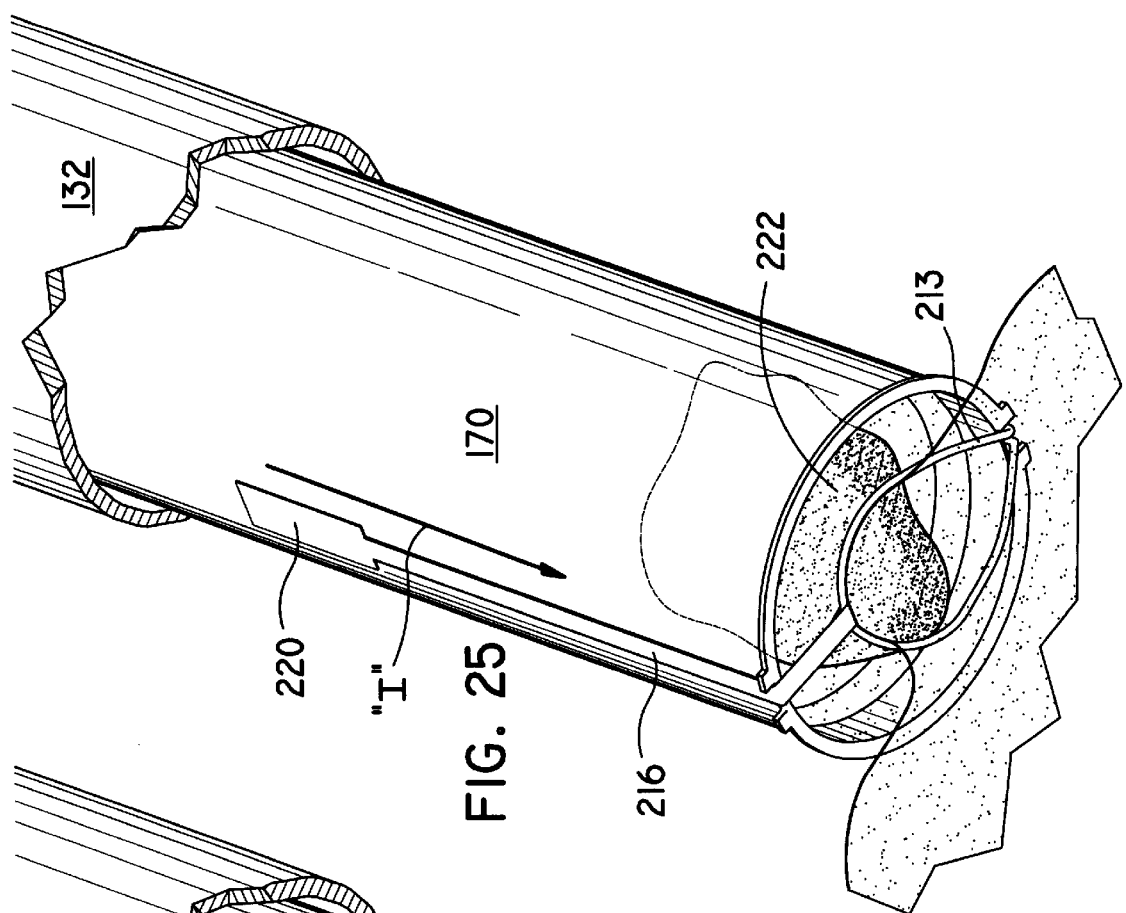
FIG. 25 is a view, similar to FIG. 24, showing deployment of the cutting loop of wire and retaining strap.
Figure 24:
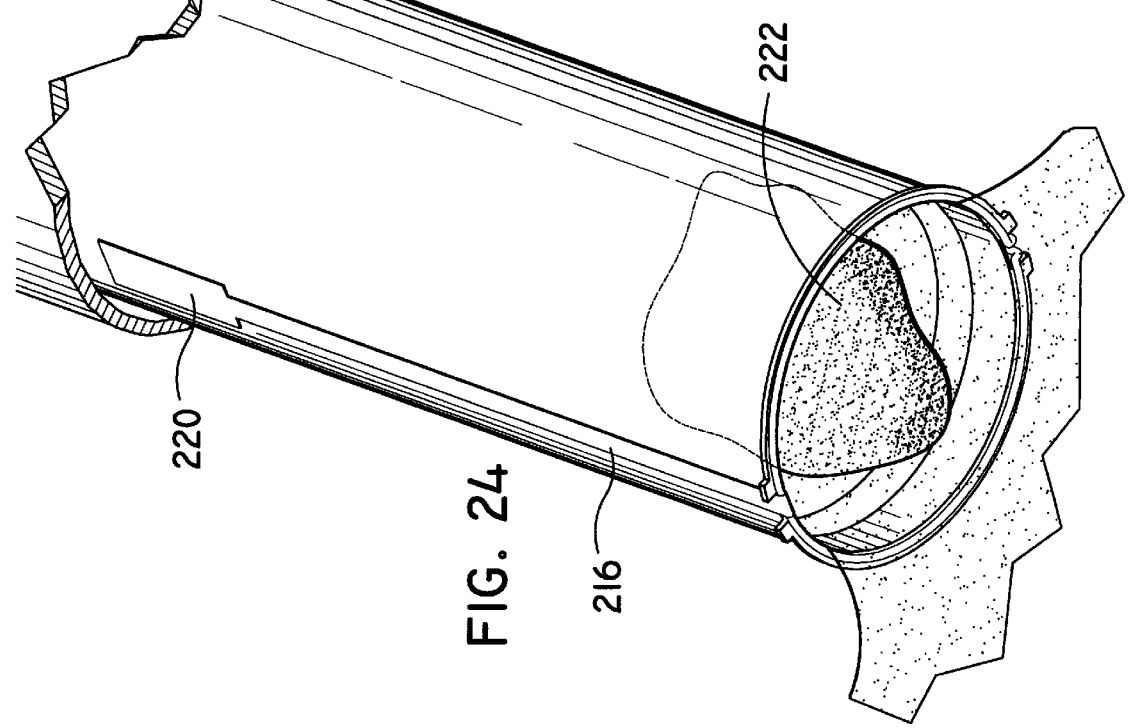
FIG. 24 is a view of the distal end of the embodiment of FIG. 1 inserted around target tissue.
Figure 27:
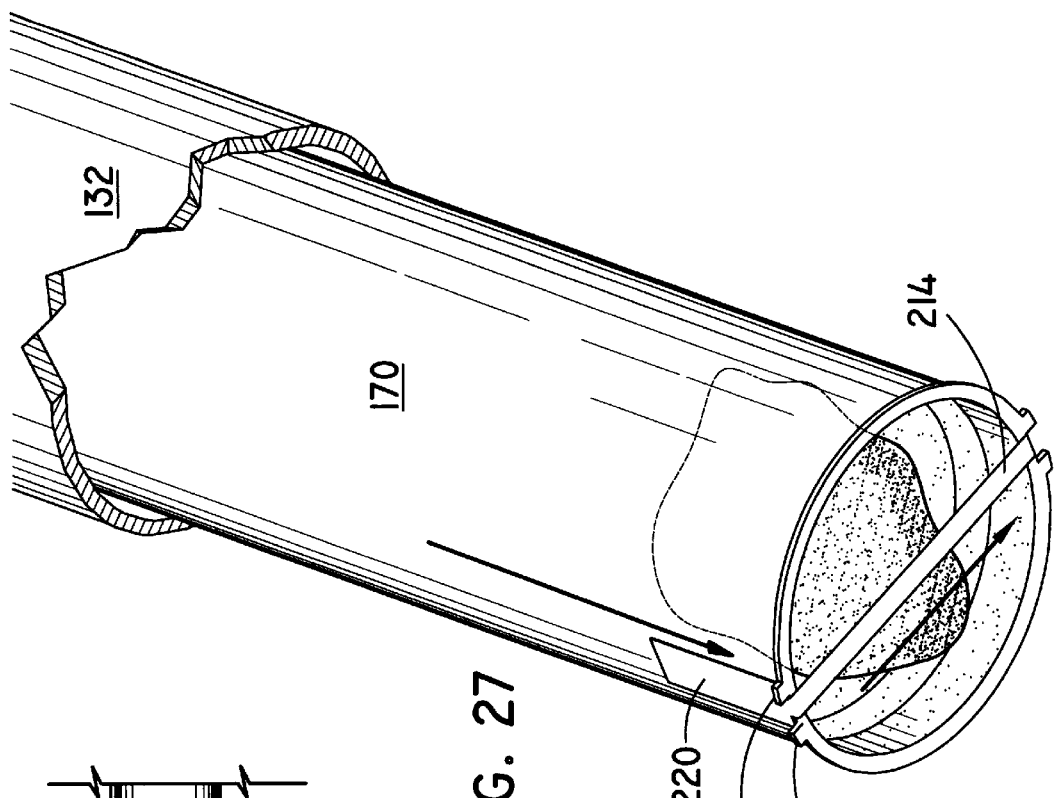
FIG. 27 is a view, similar to FIGS. 24 and 25, showing complete deployment of the cutting loop of wire and retaining strap.
Figure 26:
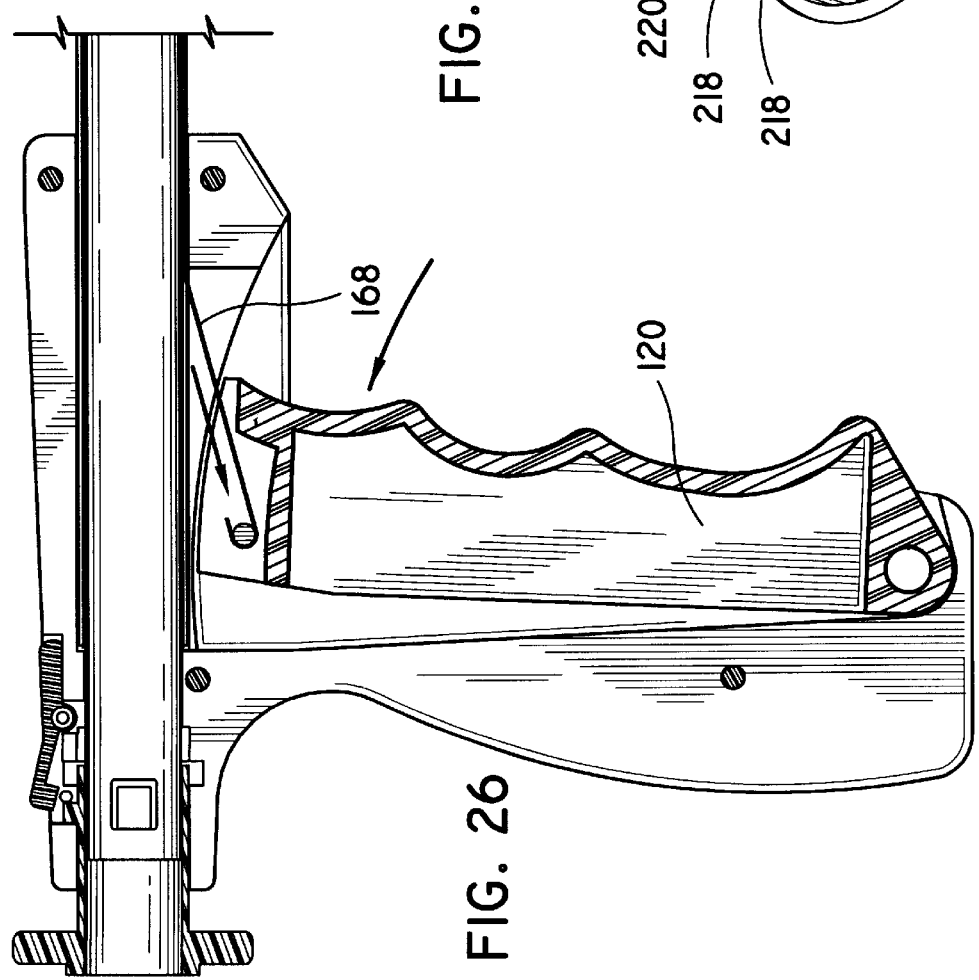
FIG. 26 is a horizontal cross-sectional view showing the proximal end of the instrument during operation of the trigger.

With central tubular shaft moved proximal of wire loop 213, transverse movement of the wire loop across the distal open end of elongated tubular sheath 170 is effected by squeezing trigger 120, as indicated by arrow "H" in FIG. 25. Upon transverse movement of wire loop 168, strap 216 is pulled distally in the direction indicated by arrow "I" in FIG. 25. With further squeezing of trigger 120, strap 214 is pulled completely across the opening at the distal end of elongated tubular sheath 170 so that tab portion 220 is prevented from further distal movement by leg portions 218 and strap 214 is pulled taut across the distal end opening of elongated tubular sheath 170. Instrument 100 may thus be removed from the patient's breast. Due to the partial obstruction of the distal end opening of elongated tubular sheath 170 by strap 214, the severed tissue core will be removed from the patient with instrument 100. To the extent necessary, the puncture wound left by instrument 100 may be closed by any suitable known suturing techniques.

Figure 28:
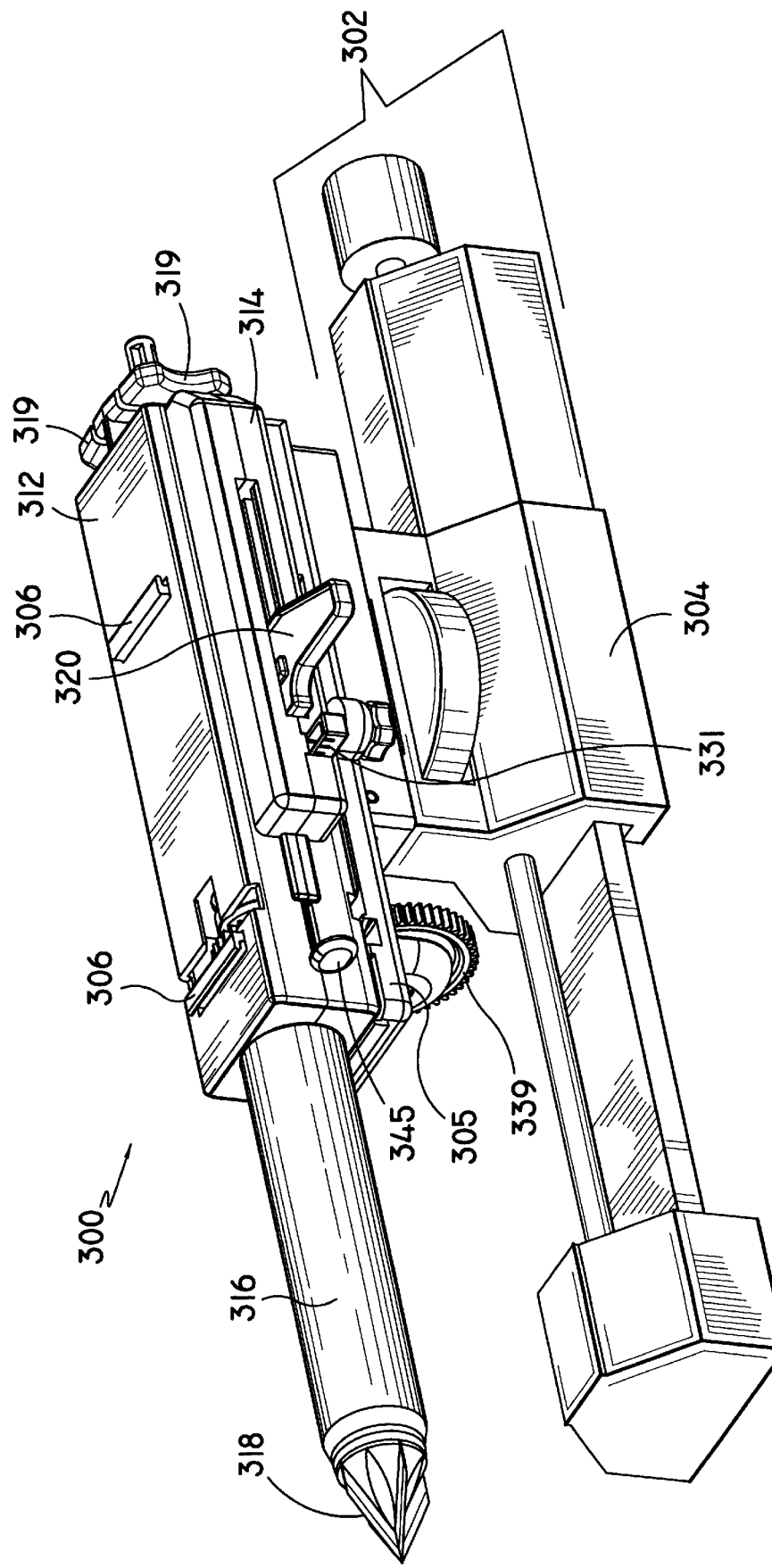
FIG. 28 is a perspective view of a further embodiment constructed in accordance with the present disclosure and mounted on a cooperative portion of a stereotactic imaging machine.

Another embodiment of the presently disclosed instrument for removing and/or taking a biopsy of target tissue and a method of its use are illustrated in FIGS. 28–40. Referring initially to FIGS. 28–30, instrument 300 is particularly adapted for use on a precision instrument positioning machine, for example, a stereotactic imaging machine. Such devices are commercially available, for example, from Lorad Corporation of Danbury, Conn. An example of such a machine is disclosed in U.S. Pat. No. 5,289,520 which issued Feb. 22, 1994 to Pellegrino et al., the contents of which are hereby incorporated by reference.

Briefly, stereotactic machines facilitate stereo x-ray imaging of a patient's breast using a three dimensional coordinate system, while the patient is in a prone position on a specially designed table. An opening is provided on the table to permit the patient's breast to be pendulantly disposed therethrough and a clamp is used to fix the exact location of the patient's pendulant breast relative to the operational components of the machine which facilitate precision interaction of instrumentation with the breast, i.e. for biopsy or tissue removal.

The overall structural and operational features of instrument 300 are very similar to those described above for instrument 100. Accordingly, the following description will focus on those features which are either unique to instrument 300 or are substantially different than corresponding elements of instrument 100. In FIG. 28, instrument 300 is shown mounted in place on the instrument positioning control mechanism of a stereotactic machine, generally designated by reference numeral 302. Stereotactic machine 302 has an instrument mount 304, the movement of which is coordinated with the imaging capabilities of the machine. The instrument mount 304 is provided with a standardized instrument or tool mounting bracket 305 to facilitate mounting of various surgical instruments which can take advantage of the precision positioning features of the stereotactic machine. This is particularly beneficial in procedures where the target tissue is not palpable. As will be readily apparent based on the disclosure herein, the cooperative structures on instrument 300 and stereotactic machine 302 may be reconfigured so that more structure is included on instrument 300 and less on machine 302, or vice versa. All that is required is that stereotactic machine 302 and instrument 300 cooperate so as to position instrument 300 as desired with respect to the target tissue.

Instrument 300 is provided with four slide mounts 306, two of which are formed on each side of housing half-sections 312 and 314 so that instrument 300 can be mounted on either side. Thus, the mechanical operational controls of instrument 300, all of which are positioned on the same side of the instrument, may be oriented to suit the preference of the personnel using the instrument during the particular procedure. It is envisioned that some of the control actuators of instrument 300 may be reconfigured so that they would be operable from a different side than the remaining control actuators. Housing half-sections 312 and 314 are preferably molded to conform to the dimensions of the stereotactic machine tool mounting bracket 305, for example, a rectangular base dimension.

Obturator 318 has a pair of resiliently formed retaining members 319 each of which include a shoulder portion 321 which engages a cut-out portion of the proximal end wall of housing half-section 314 to maintain obturator 318 in place during insertion of instrument 300.

Figure 31:
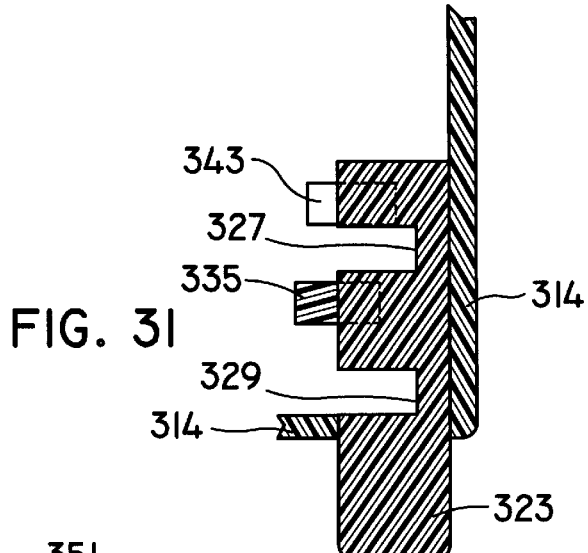
FIG. 31 is a cross-sectional view taken along section line 31—31 of FIG. 29.

As shown in FIGS. 29–31, a firing lockout mechanism is provided to prevent premature movement of the cutting wire before obturator 318 and central tubular shaft 338 are properly positioned relative to the wire loop positioned at the distal end of wire 368 (similar to loop 213 of wire 168). The firing lockout mechanism includes a safety lockout member 323 and a control member, such as slide bar member 341. Lockout member 323 is slidably received in a cutout 325 formed in a sidewall of housing half-section 314 and has a pair of slotted keyways 327 and 329 formed thereon. Also provided on lockout member 323 are raised portions 331 which provide tactile indication to the user of the relative positioning of lockout member 323 during a two-stage lockout release process described below.

Trigger 320 is provided with a retaining pin 333 which has a pair of bores formed therethrough to receive and frictionally retain wire loop 368. A latch portion 335 is formed extending from the distal side of trigger 320 which is configured and dimensioned to interact with lockout member 323 and specifically to slide in keyway 327.

Central tubular shaft 338 is fitted at a proximal end with gear collar 337, the teeth of which are designed to mesh with the teeth of gear 339 which is manually driven by a drive mechanism. Alternatively, a powered drive mechanism may be provided on stereotactic machine 302. A slide bar 341 cradles gear collar 337 to permit rotational movement thereof while controlling the axial alignment of central tubular shaft 338 within housing half-sections 312 and 314. Slide bar 341 is provided with a latch portion 343 formed at a proximal end thereof. At the distal end, slide bar 341 has actuator button 345 to facilitate proximal movement of slide bar 341 by the user. Another feature of slide bar 341 is a diagonal groove 347 which is formed in the side surface adjacent the proximal end of the slide bar to permit wire loop 368 to slidably pass therethrough, as best seen in FIG. 29.

The two stage lockout process of lockout member 323 is best shown in FIGS. 31–35 in conjunction with FIGS. 36–40. Upon the insertion of the instrument into the patient, FIGS. 36 and 37, it is desirable to maintain the relative axial positioning of central tubular shaft 338 with respect to outer tubular sheath 332 as well as to prevent firing of trigger 320. Both of these preventive goals are accomplished when obturator 318 is positioned within the instrument and lockout member 323 is maintained in its initial position as shown in FIG. 29 by obturator member 318 and shoulder portion 349 of lockout member 323 biasing against the outer wall of housing half-section 314. In this position, keyways 327 and 329 of lockout member 323 are maintained out of alignment with slide bar 341 and latch portion 335 of trigger 320, respectively.

Figure 37:
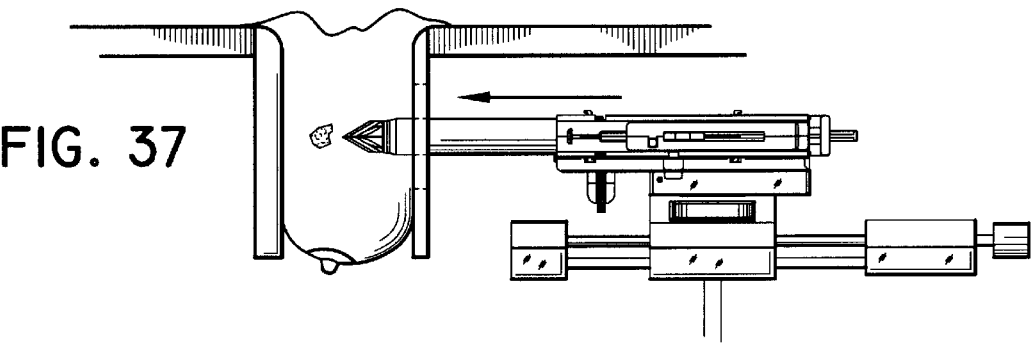
FIG. 37 is a view, similar to FIG. 36, demonstrating a further sequence of operation of the embodiment of FIG. 28.
Figure 38:
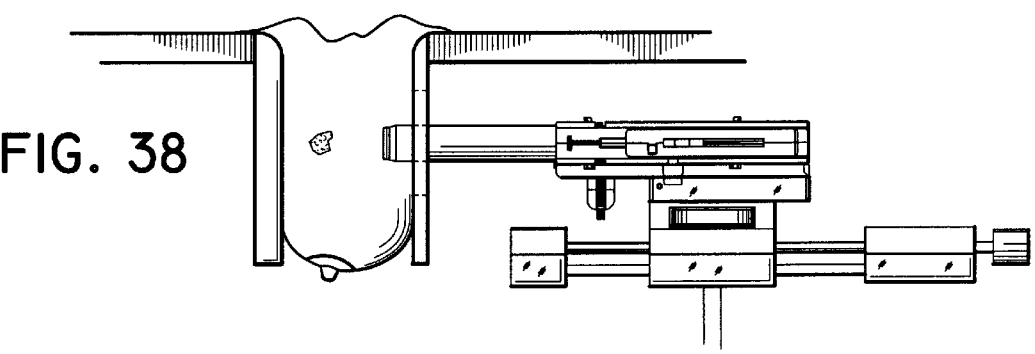
FIG. 38 is a view, similar to FIG. 36, demonstrating a further sequence of operation of the embodiment of FIG. 28.
Figure 39:
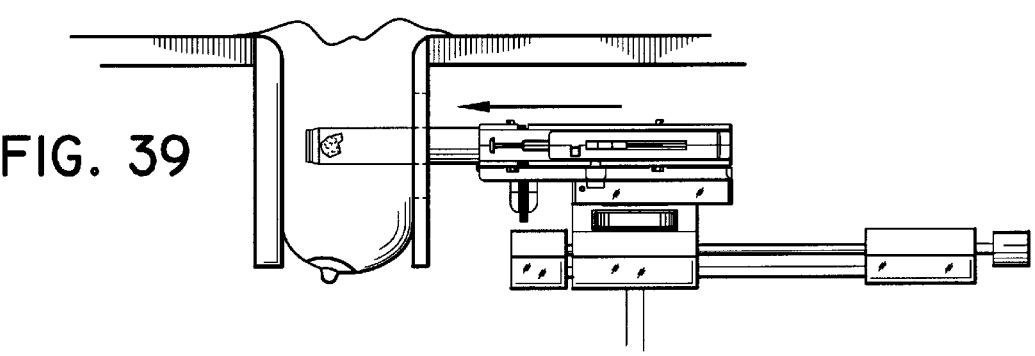
FIG. 39 is a view, similar to FIG. 36, demonstrating a further sequence of operation of the embodiment of FIG. 28.
Figure 40:
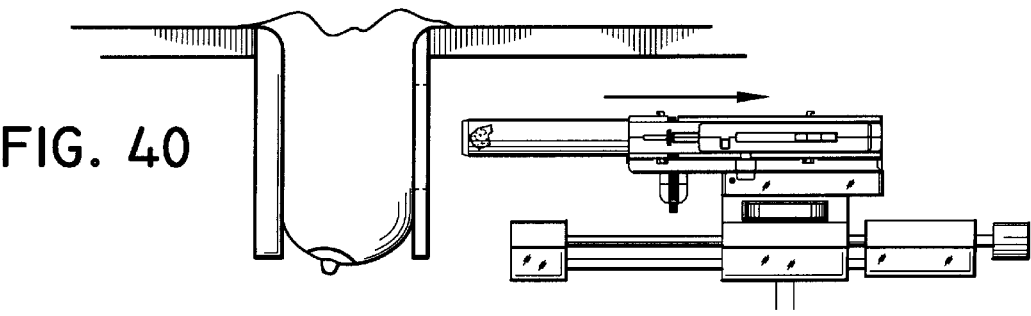
FIG. 40 is a view, similar to FIG. 36, demonstrating a further sequence of operation of the embodiment of FIG. 28.

After insertion of instrument 300 into the patient as shown in FIG. 37, preferably by automated movement of instrument mount 304 by a drive mechanism on stereotactic machine 300, obturator 318 is removed (FIGS. 29 and 38) by pressing radially inwardly on retaining members 319 to disengage the retaining members from shoulder portions 321 from the proximal end wall of housing half-section 314. With obturator 318 removed from the instrument, as shown in FIG. 32, lockout member 323 is free to move transversely toward the central longitudinal axis of instrument 300.

Figure 32:
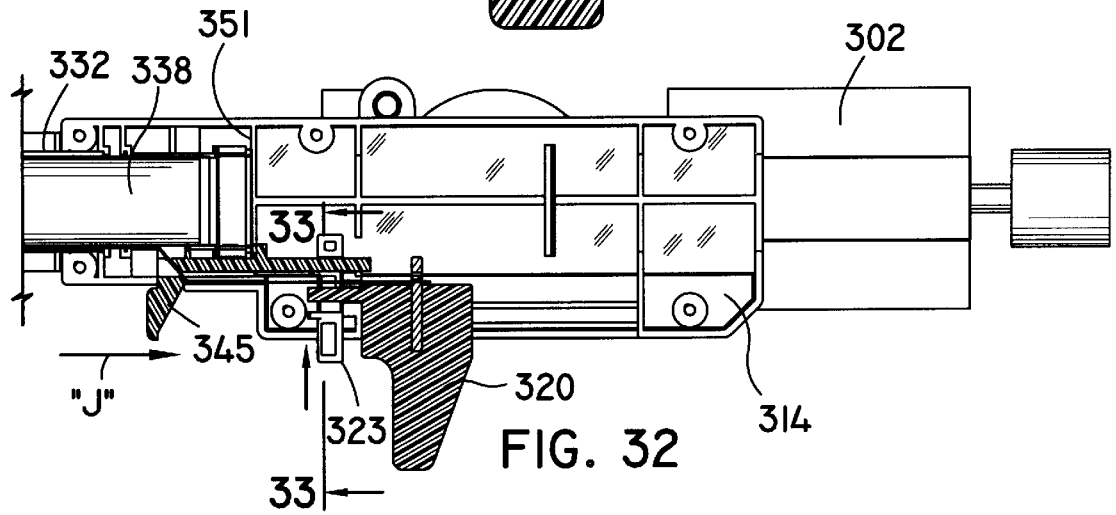
FIG. 32 is a cross-sectional top view of the proximal end of the embodiment of FIG. 28.
Figure 33:
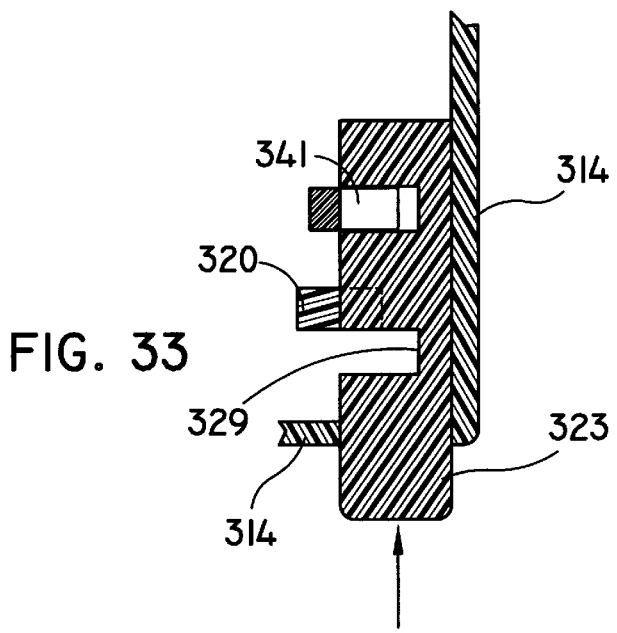
FIG. 33 is a cross-sectional view taken along section line 33—33 of FIG. 32.

The first stage of releasing lockout member 323, illustrated in FIG. 32, is accomplished when the user pushes lockout member 323 inwardly toward the center of the instrument. A tactile indication is felt by the user when the first raised portion 331 passes over the side wall of housing half-section 314. Actuator button 345 is moved proximally, as indicated by arrow "J" in FIG. 32, to effect proximal movement of central tubular shaft 138. This proximal movement is limited by partition 351 formed transversely across housing half-section 314. During proximal movement of slide bar 341, latch portion passes through keyway 327 and prevents further transverse movement of lockout member 323 until latch portion 343 passes completely through keyway 327.

Figure 34:
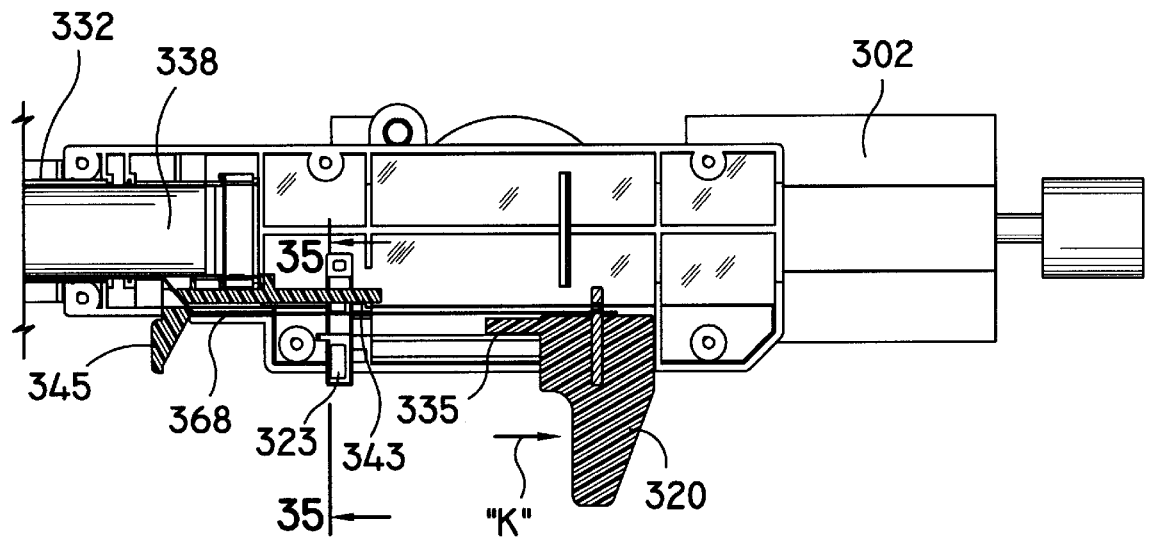
FIG. 34 is a view, similar to FIG. 32, showing the operation of various elements of the embodiment of FIG. 28.
Figure 35:
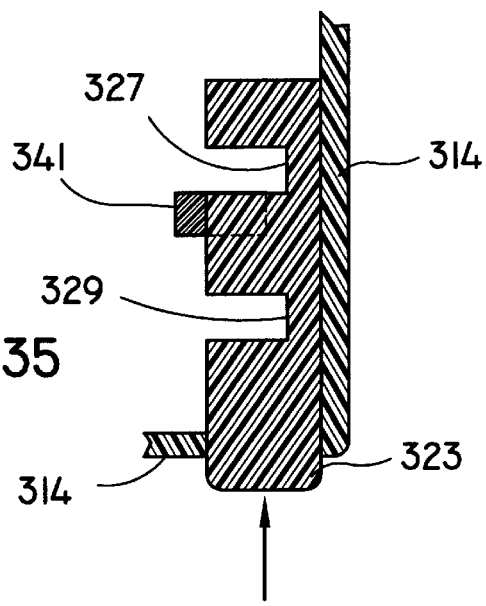
FIG. 35 is a cross-sectional view taken along section line 35—35 of FIG. 34.
Figure 36:
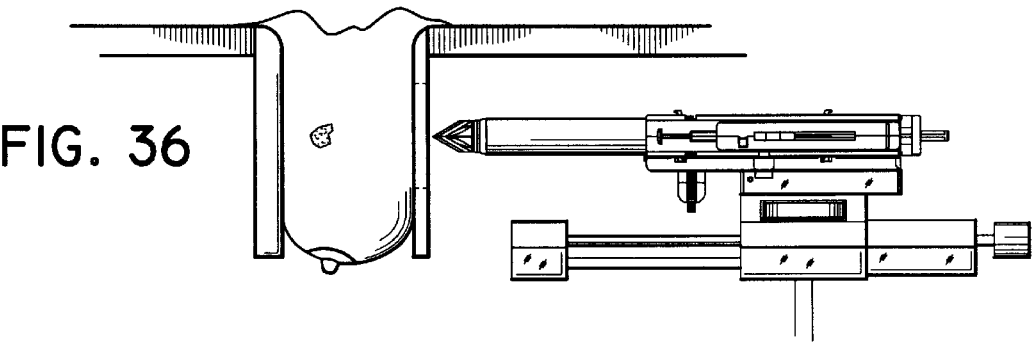
FIG. 36 is a view demonstrating a sequence of operation of the embodiment of FIG. 28 as mounted on a cooperative portion of a stereotactic imaging machine.

After proximal movement of central tubular shaft 38, lockout member 323 is again pushed transversely inward (see FIGS. 32 and 33) until the user feels another tactile indication, resulting from the second raised portion 331 crossing over the side wall of housing half-section 314. In this position, as shown in FIGS. 34 and 35, latch 335 of trigger 320 is aligned with keyway 329. Trigger 320 is moved proximally in the direction of arrow "K". Also when lockout member 323 is in the orientation shown in FIG. 34, latch portion 343 of slide bar 341 is in engagement with lockout member 323 to prevent distal movement of slide bar 341 and, therefore, central tubular shaft 338, during firing of trigger 320.

Figure 41:
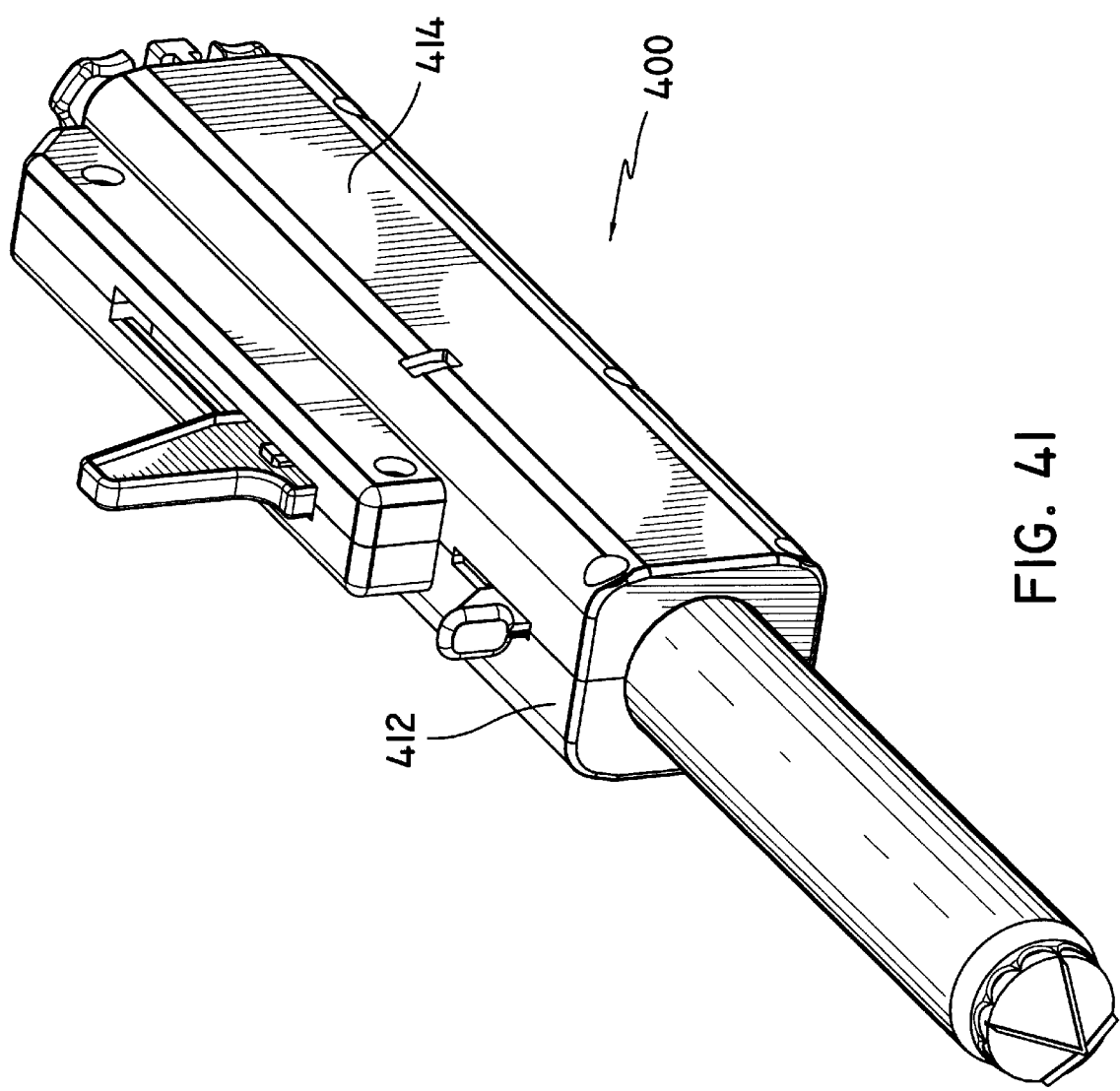
FIG. 41 is a perspective view of a further embodiment of a tissue removing apparatus constructed in accordance with the present disclosure.

A further embodiment of a tissue removing instrument is shown in FIG. 41. Instrument 400 is similar to the embodiment of FIGS. 28–40 and is designed to be inserted and used manually by a surgeon, rather than in conjunction with a stereotactic machine. The handle of instrument 400 includes handle half-sections 412 and 414 which are molded to a dimension suitable for being held in the palm of either the user's left or right hands. The control mechanisms of instrument 400 may be the same as those for instrument 300 or lockout member 323 may be eliminated as shown in FIG. 41. The basic manner of usage of instrument is the same as that for instrument 300.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A biopsy apparatus which comprises:
   a coring cannula having a proximal portion and a distal portion which defines a tissue receiving cavity in communication with an opening, the coring cannula including a sharpened cutting edge disposed at the distal portion;
   an elongated penetrating member having a plurality of discrete planar cutting surfaces each having a sharpened cutting edge formed thereon extending from a distal end of the elongated penetrating member, the elongated penetrating member being disposed within the coring cannula such that the cutting edges of the plurality of the discrete planar cutting surfaces extend beyond a distal end of the distal portion of the coring cannula; and
   a tissue cutting member having a cutting portion which moves transverse to the coring cannula in proximity to the opening to effect severing of a tissue sample disposed in the tissue receiving cavity.

2. A biopsy apparatus according to claim 1, wherein the distal end of the penetrating member includes a tapered surface and at least one of the plurality of cutting surfaces is disposed substantially parallel to the tapered surface.

3. A biopsy apparatus according to claim 2, wherein the length of the at least one of the sharpened cutting edges of the plurality of cutting surfaces is less than the length of the tapered surface.

4. A biopsy apparatus according to claim 1, wherein the coring cannula is rotatably disposed about the penetrating member.

5. A biopsy apparatus according to claim 1, wherein the plurality of cutting surfaces are defined by a plurality of discrete blade members secured to the distal end of the penetrating member.

6. A biopsy apparatus which comprises:
   a housing;
   an elongated coring cannula which includes a proximal portion and a distal portion, wherein the distal portion extends from the housing and defines a tissue receiving cavity in communication with an opening, the coring cannula includes a sharpened cutting edge disposed at the distal portion;
   an elongated penetrating member which includes a plurality of discrete cutting blades extending from a distal end thereof, wherein at least two of the plurality of discrete cutting blades are disposed in the same plane, the elongated penetrating member being disposed within the elongated coring cannula such that the plurality of discrete cutting blades extend beyond a distal end of the elongated coring cannula distal portion; and a tissue cutting member operatively associated with the housing, the tissue cutting member including a cutting portion which moves transverse to the coring cannula in proximity to the opening to effect severing of a tissue sample disposed in the tissue receiving cavity.

7. A biopsy apparatus according to claim 6, which further comprises an actuator operatively connected to the tissue cutting member whereby the actuator facilitates the transverse movement of the cutting portion.

8. A biopsy apparatus according to claim 6, wherein the distal end of the penetrating member includes a tapered surface and at least one of the plurality of discrete cutting blades is disposed substantially parallel to the tapered surface.

9. A biopsy apparatus according to claim 8, wherein the length of the at least one of the plurality of discrete cutting blades is less than the length of the tapered surface.

10. A biopsy apparatus according to claim 6, wherein the coring cannula is rotatably disposed about the penetrating member.

11. A biopsy apparatus which comprises:

a housing;

an elongated coring cannula which includes a proximal portion and a distal portion, wherein the distal portion extends from the housing and defines a tissue receiving cavity in communication with an opening, the coring cannula includes a sharpened cutting edge disposed at the distal portion;

an elongated penetrating member including a head portion and at least two discrete co-planar cutting surfaces extending from a distal end of the head portion, the cutting surfaces each having a sharpened cutting edge formed thereon;

the elongated penetrating member being disposed within the coring cannula such that the plurality of cutting surfaces extend beyond a distal end of the distal portion of the coring cannula; and a tissue cutting member having a cutting portion which moves transverse to the coring cannula in proximity to the opening to effect severing of a tissue sample disposed in the tissue receiving cavity.

12. A biopsy apparatus according to claim 11, wherein the distal end of the head portion includes a tapered surface and the at least two discrete co-planar cutting surfaces are disposed substantially parallel to the tapered surface.

13. A biopsy apparatus according to claim 12, wherein the individual length of each of the at least two discrete co-planar cutting surfaces is less than the length of the tapered surface.

14. A biopsy apparatus according to claim 11, wherein the coring cannula is rotatably disposed about the penetrating member.

15. A biopsy apparatus according to claim 11, wherein the at least two discrete co-planar cutting surfaces are defined by discrete blade members secured to the distal end of the head portion.

* * * * *